US010934224B2

(12) United States Patent
Wecker

(10) Patent No.: US 10,934,224 B2
(45) Date of Patent: Mar. 2, 2021

(54) PRODUCTION OF ARGININE-RICH PROTEINS FROM WASTEWATER AND USE AS A FERTILIZER

(71) Applicant: Genebiologics, LLC, Boulder, CO (US)

(72) Inventor: Matt S. A. Wecker, Boulder, CO (US)

(73) Assignee: Genebiologics, LLC, Boulder, CO (US)

( * ) Notice: Subject to any disclaimer, the term of this patent is extended or adjusted under 35 U.S.C. 154(b) by 226 days.

(21) Appl. No.: 16/040,327

(22) Filed: Jul. 19, 2018

(65) Prior Publication Data
US 2018/0319713 A1    Nov. 8, 2018

Related U.S. Application Data

(63) Continuation-in-part of application No. PCT/US2017/014169, filed on Jan. 19, 2017.
(Continued)

(51) Int. Cl.
*C05C 11/00* (2006.01)
*A01H 3/04* (2006.01)
(Continued)

(52) U.S. Cl.
CPC ............ *C05C 11/00* (2013.01); *A01H 3/04* (2013.01); *C02F 9/00* (2013.01); *C05D 9/00* (2013.01);
(Continued)

(58) Field of Classification Search
None
See application file for complete search history.

(56) References Cited

U.S. PATENT DOCUMENTS 6,987,011 B1 *   1/2006   Reid ................... C12P 7/42
                                                   435/135
8,383,363 B1 *   2/2013   Ueda ................. C12P 13/04
                                                    435/41
(Continued)

OTHER PUBLICATIONS

Dietz, G. P. H., et al., "Synthesis of Cell-Penetrating Peptides and Their Application in Neurobiology," from: Methods in Molecular Biology:, vol. 399: Neuroprotection Methods and Protocols, Borsello, T., ed., Humana Press, Totowa, NJ, USA, p. 181-198 (2007) Year: 2007).*
(Continued)

*Primary Examiner* — Chester T Barry
(74) *Attorney, Agent, or Firm* — Leydig, Voit & Mayer, Ltd.

(57) ABSTRACT

Disclosed are methods to convert nitrogen in a wastewater stream to an arginine-enriched polypeptide, which includes supplying a nitrogen-enriched wastewater stream; culturing an organism in the waste stream that produces an arginine-enriched polypeptide to produce the arginine-enriched polypeptide; and removing the produced arginine-enriched polypeptide from the wastewater stream to create a processed wastewater stream. The methods also include a method to make an arginine-enriched polypeptide enriched fertilizer by flowing the effluent from the culturing step over a cation exchange material to allow binding of the arginine enriched polypeptide to the cation exchange material; and collecting arginine-enriched polypeptide to form the arginine-enriched polypeptide enriched fertilizer. The method also includes enhancing the growth or production of a plant using the fertilizer containing the arginine-enriched polypeptide.

19 Claims, 11 Drawing Sheets

Specification includes a Sequence Listing.

Related U.S. Application Data

(60) Provisional application No. 62/280,551, filed on Jan. 19, 2016.

(51) Int. Cl.

| | | |
|---|---|---|
| *C05F 11/02* | (2006.01) | |
| *C05F 9/04* | (2006.01) | |
| *C05D 9/00* | (2006.01) | |
| *C02F 9/00* | (2006.01) | |
| *C12P 21/00* | (2006.01) | |
| *C02F 1/42* | (2006.01) | |
| *C02F 3/28* | (2006.01) | |
| *C02F 3/30* | (2006.01) | |
| *C02F 101/16* | (2006.01) | |
| *C02F 103/00* | (2006.01) | |
| *C02F 103/26* | (2006.01) | |
| *C02F 103/34* | (2006.01) | |

(52) U.S. Cl.
CPC ............... *C05F 9/04* (2013.01); *C05F 11/02* (2013.01); *C12P 21/00* (2013.01); *C02F 1/42* (2013.01); *C02F 3/28* (2013.01); *C02F 3/302* (2013.01); *C02F 2001/425* (2013.01); *C02F 2101/16* (2013.01); *C02F 2103/007* (2013.01); *C02F 2103/26* (2013.01); *C02F 2103/34* (2013.01); *C02F 2301/046* (2013.01); *Y02A 40/20* (2018.01); *Y02P 20/145* (2015.11)

(56) References Cited

U.S. PATENT DOCUMENTS

| | | | | |
|---|---|---|---|---|
| 10,479,969 | B2* | 11/2019 | Kim | C12M 21/02 |
| 2005/0205490 | A1* | 9/2005 | Park | C02F 3/348 |
| | | | | 210/605 |
| 2005/0283003 | A1* | 12/2005 | Spudich | G01N 33/552 |
| | | | | 530/416 |
| 2010/0322839 | A1* | 12/2010 | Chung | C02F 1/5254 |
| | | | | 423/302 |
| 2012/0065124 | A1* | 3/2012 | Morishita | A61P 43/00 |
| | | | | 514/1.1 |
| 2014/0076799 | A9* | 3/2014 | Liu | C02F 3/08 |
| | | | | 210/605 |
| 2014/0259212 | A1* | 9/2014 | Plesch | C12P 1/00 |
| | | | | 800/278 |
| 2016/0185816 | A1* | 6/2016 | Charlton | C07K 1/18 |
| | | | | 435/226 |
| 2017/0247751 | A1* | 8/2017 | Humphrey | C12Q 1/6825 |

OTHER PUBLICATIONS

Futaki, S., T. Suzuki; W Ohashi, T, Yagami, S. Tanaka; K. Ueda, and Y. Sugiura, Arginine-rich peptides an abundant source of membrane-permeable peptides having potential as carriers for intracellular protein delivery. Journal of Biological Chemistry, 2001. 276(8): p. 5836-5840.

Qi, X., T. Droste and C.C. Kao, Cell-penetrating peptides derived from viral capsid proteins. Molecular plant-microbe interactions, 2011. 24(1): p. 25-36.

Peeters, E., P. Nguyen Le Minh, M. Foulquie-Moreno and D. Charlier, Competitive activation of the *Escherichia coli* argO gene coding for an arginine exporter by the transcriptional regulators Lrp and ArgP. Molecular microbiology, 2009. 74(6): p. 1513-1526.

Mitchell, D.J., L. Steinman, D.T. Kim, C.G. Fathman and J.B. Rothbard, Polyarginine enters cells more efficiently than other polycationic homopolymers. The Journal of Peptide Research, 2000. 56(5): p. 318-325.

Fuchs, S.M. and R.T. Raines, Polyarginine as a multifunctional fusion tag. Protein science, 2005. 14(6): p. 1538-1544.

Wender, P.A., D,J. Mitchell, K. Pattabiraman, E.T. Pelkey, L. Steinman, and J.B. Rothbard, The design, synthesis, and evaluation of molecules that enable or enhance cellular uptake: peptoid molecular transporters. Proceedings of the National Academy of Sciences, 2000. 97(24): p. 13003-13008.

Rothbard, J.B., S. Garlington, Q. Lin, T. Kirschberg, E. Kreider, P.L. Mcgrane, . . . P.A. Khavari, Conjugation of arginine oligomers to cyclosporin A facilitates topical delivery and inhibition of inflammation. Nat Med, 2000. 6(11): p. 1253-1257.

Chang, M., J.-C. Chou and H.-J. Lee, Cellular internalization of fluorescent proteins via arginine-rich intracellular delivery peptide in plant cells. Plant and cell physiology, 2005. 46(3): p. 482-488.

\* cited by examiner

Table 1 Increased germination and biomass yield of Arabidopsis thaliana due to the addition of polyarginine or arginine to N-replete growth media.

| Medium | Conc arg | wet wt | #seeds | ug ww/seed | x-fold biomass | germinated | % germ | x-fold germ | #cotyledons | root length | stem length |
|---|---|---|---|---|---|---|---|---|---|---|---|
| MS Arg | 0 | 22 | 9 | 2.4 | 1.0 | 1 | 11% | 1 | 0 | 1 | 0 |
|  | 10 | 15 | 8 | 1.9 | 0.8 | 0 | 0% | 0 | 0 | 1 | 0 |
|  | 30 | 27 | 9 | 3.0 | 1.2 | 0 | 0% | 0 | 0 | 0 | 0 |
|  | 100 | 75 | 9 | 8.3 | 3.4 | 9 | 100% | 9 | 9 | 2 | 3 |
|  | 300 | 83 | 8 | 10.4 | 4.2 | 7 | 88% | 8 | 7 | 2 | 3 |
| 0.1MS Arg | 0 | 29 | 9 | 3.2 | 1.0 | 1 | 11% | 1 | 0 | 1 | 0 |
|  | 10 | 32 | 8 | 4.0 | 1.2 | 4 | 50% | 5 | 0 | 1 | 0 |
|  | 30 | 17 | 9 | 1.9 | 0.6 | 2 | 22% | 2 | 2 | 1 | 1 |
|  | 100 | 93 | 9 | 10.3 | 3.2 | 9 | 100% | 9 | 9 | 2.5 | 2 |
|  | 300 | 42 | 8 | 5.3 | 1.6 | 8 | 100% | 9 | 8 | 3 | 2 |
| H2O Arg | 0 | 10 | 8 | 1.3 | 1.0 | 0 | 0% | - | 0 | 0 | 0 |
|  | 10 | 15 | 8 | 1.9 | 1.5 | 2 | 25% | - | 0 | 1 | 0 |
|  | 30 | 17 | 8 | 2.1 | 1.7 | 1 | 13% | - | 0 | 1 | 0 |
|  | 100 | 12 | 9 | 1.3 | 1.1 | 1 | 11% | - | 0 | 1 | 0 |
|  | 300 | 9 | 9 | 1.0 | 0.8 | 1 | 11% | - | 1 | 1 | 1 |
|  | Conc Arg70 |  |  |  |  |  |  |  |  |  |  |
| MS Arg70 | 0 | 19 | 8 | 2.4 | 1.0 | 2 | 25% | 1 | 0 | 1 | 0 |
|  | 10 | 10 | 9 | 1.1 | 0.5 | 1 | 11% | 0 | 0 | 1 | 0 |
|  | 30 | 17 | 8 | 2.1 | 0.9 | 2 | 25% | 1 | 1 | 1 | 1 |
|  | 100 | 54 | 8 | 6.8 | 2.8 | 8 | 100% | 4 | 8 | 2 | 2 |
|  | 300 | 60 | 8 | 7.5 | 3.2 | 8 | 100% | 4 | 8 | 2 | 2 |
| 0.1MS Arg70 | 0 | 11 | 8 | 1.4 | 1.0 | 1 | 13% | 1 | 0 | 1 | 0 |
|  | 10 | 92 | 8 | 11.5 | 8.4 | 6 | 75% | 6 | 6 | 2 | 2 |
|  | 30 | 25 | 8 | 3.1 | 2.3 | 3 | 38% | 3 | 1 | 1 | 1 |
|  | 100 | 28 | 9 | 3.1 | 2.3 | 2 | 22% | 2 | 1 | 1 | 1 |
|  | 300 | 37 | 9 | 4.1 | 3.0 | 1 | 11% | 1 | 1 | 1 | 1 |
| H2O Arg70 | 0 | 6 | 8 | 0.8 | 1.0 | 1 | 13% | 1 | 0 | 1 | 0 |
|  | 10 | 14 | 8 | 1.8 | 2.3 | 1 | 13% | 1 | 0 | 1 | 0 |
|  | 30 | 15 | 8 | 1.9 | 2.5 | 2 | 25% | 2 | 0 | 1 | 0 |
|  | 100 | 51 | 8 | 6.4 | 8.5 | 6 | 75% | 6 | 6 | 3 | 1 |
|  | 300 | 18 | 8 | 2.3 | 3.0 | 2 | 25% | 2 | 0 | 1 | 0 |

Fig. 6

Table 2. The inhibition of the binding of Cobalt to CM sepharose by polyarginine.

| test | trial 1 | trial 2 | trial 3 | average | stdev.p |
|---|---|---|---|---|---|
| blank | -0.0005 | | 0.0002 | -0.0002 | 0.0004 |
| Nothing added | 0.0162 | 0.0187 | 0.018 | 0.0176 | 0.0011 |
| Arginine | 0.0198 | 0.0238 | 0.0212 | 0.0216 | 0.0017 |
| Polyarginine | 0.0071 | 0.0104 | 0.0052 | 0.0076 | 0.0021 |

Fig. 7

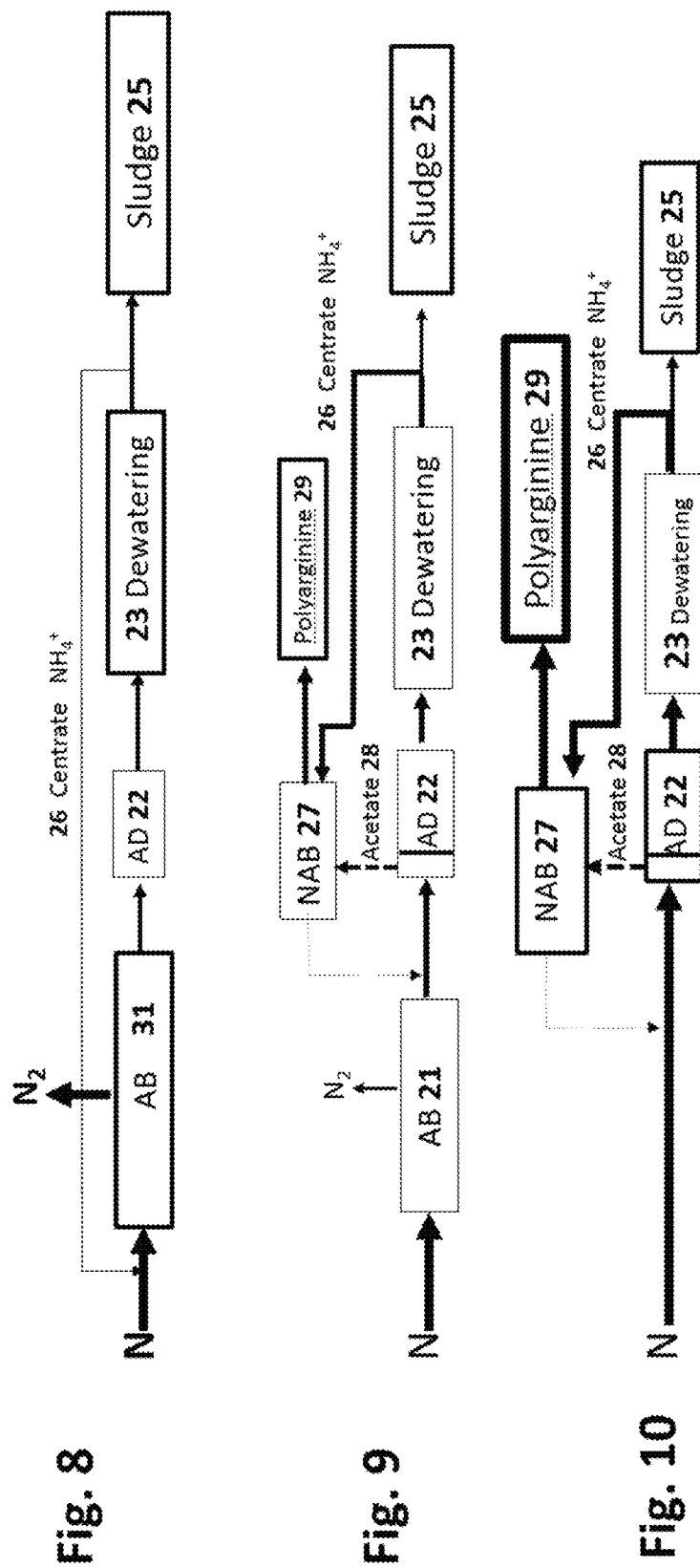

PRODUCTION OF ARGININE-RICH PROTEINS FROM WASTEWATER AND USE AS A FERTILIZER

CROSS-REFERENCE TO RELATED APPLICATIONS

This application is a continuation-in-part application filed under 35 U.S.C. § 111(a) which claims the benefit of pending PCT Application No. PCT/US17/14169, filed Jan. 19, 2017, which in turn claims benefit from U.S. provisional application Ser. No. 62/280,551, filed 19 Jan. 2016. Each application is hereby incorporated by reference in its entirety.

BACKGROUND

The imbedded energy used in the production of fertilizer currently accounts for approximately 30% of all energy used in commercial farming. Furthermore, ammonia for use in fertilizer is currently principally made using natural gas, with about 1.3% of all natural gas used in the United States being directed to ammonia manufacture. With concerns over the induction of global warming by releasing $CO_2$ through the burning of fossil fuels such as natural gas, there is great interest in producing fertilizers that are renewable in origin, for example, the use of compost and, as a second example, the use of cyanobacteria inoculations into soil. Current farming practices are not always amenable to the form such renewable fertilizers take. As such there is interest in the production of concentrated fertilizers that are inherently renewable.

Most current fertilizer is sold as $NH_3$ for injection into the ground, or as urea or urea ammonium nitrate. Urea is easy to apply but typically results in 10-50% loss of nitrogen (N) due to run-off and volatilization. Current slow-release fertilizers use a variety of means to slow release of ammonium and $NO_3^-$, including reaction of urea with formaldehyde, coating urea with polymers (wax/sulfur or plastic), adding antibiotics along with the urea, and inhibiting urease or nitrification enzymes by adding inhibitors or chelating metals required for their activity. Cheaper polyurethane slow-release versions of urea are often not completely broken down, have 20% less N than urea, and leave some of the N unavailable. Even so they still typically cost 30-70% more than urea itself. Such enhanced-efficiency fertilizers can limit $NH_3$ and $N_2O$ emissions by ~40-60% depending upon formulation and soil type. With 14,000 compounds having been tested for use as urease inhibitors (prior to 2003) there is strong market pressure to develop new, sustainable, environmentally-benign, slow-release fertilizers such as chitosan, sodium alginate, starch derivatives, cellulose derivatives, lignin, agricultural residues, biochar, and polydopamine. However, because the coatings themselves are expensive, formulations are typically 2.5-8 times the cost of urea and are not broadly sold.

Current fertilizers, generally consisting of $NH_3$ and urea, do not bind soil—as a result much of the fertilizer is lost due to run-off as $NO_3^-$ or vaporization as $NH_3$. Adding excess fertilizer during application in order to compensate for the loss leads to increased N loss and burning of plants.

Slaughterhouse waste or tanning waste, which contains a strong protein fraction, is frequently used as a N fertilizer. Arginine has been a known fertilizer for more than 100 years, and is currently marketed by SweTree Technologies (Sweden) as ArGrow. A difference with the current invention is that the current invention uses polymers of arginine, since each additional arginine residue of the polymer causes the collective polymer to bind more tightly than the sum of its independent monomers, and because of this the polymer can be designed with specific N release characteristics. A second difference is that breakdown of the polymer requires the additional step of enzyme activity in order for it to be released from the soil. A third difference is that the polymer is by weight more N-rich than the monomer alone, since each addition of a monomer results in the loss of one water.

On a second level, wastewater treatment is an energy-intensive process that uses ~2% of U.S. electrical energy production in order to convert nitrogenous wastes to nitrogen gas, methane and biosolids. These products are of negative, or very low commercial value. Thus municipal, agricultural and industrial waste streams are largely untapped N resources. This has brought some interest in the use of wastewater for the production of fuels, oils, ethanol, methanol and algal biosolids. However, the only product consistently produced from wastewater is natural gas; even so much of the natural gas produced from wastewater is flared off, which the production of natural gas merely being a method of pulling carbon out of solution and conversion into $CO_2$.

In order to meet increasingly strict regulatory criteria, (for instance, the State of Colorado Reg31 Colorado Water Quality Control Act) many WWTPs (Wastewater treatment plants) are incorporating treatment designs that reflect newer technical approaches such as the Anammox, Simultaneous Nitrification and Denitrification (SND) and Moving Bed Biofilm Reactor (MBBR) systems. None of these systems produces a useful product from wastewater N, and all involve attentive regulation of oxygen and careful staging with careful separation of different organism classes.

Of these, Anammox reactors have been shown to be 60% more energy efficient than traditional treatment systems although they do require O2 during a partial nitrification stage. Recent Anitamox systems utilizing moving-bed technology have more consistent productivity. But, Anammox reactors require low C:N ratios and elevated temperatures, and their bacteria are slow-growing leading to concerns of keeping reactors productive. Anammox reactors are sensitive to $NO_3$, $O_2$, $NH_3$, salinity, heavy metals, phosphate and sulfide concentrations and are typically controlled for the ratio of $NO_2:NH_3$, and inorganic carbon to $NH_3$.

The Ostara Pearl system produces a phosphate-rich mineralized fertilizer (struvite) from WVVTP streams. Because of low N levels, struvite is complementary to high-N fertilizers such as polyarginine. Struvite may contain heavy metals, and be more suitable for non-farming applications such as golf courses.

The present invention is directed toward overcoming one or more of the problems discussed above.

SUMMARY OF THE EMBODIMENTS

The present invention includes a method to convert nitrogen in a wastewater stream to an arginine-enriched polypeptide, where the method includes: supplying a nitrogen-containing wastewater stream; culturing an organism in the waste stream that produces an arginine-enriched polypeptide; and removing the produced arginine-enriched polypeptide from the wastewater stream to create a processed wastewater stream. The methods can result in an overall reduced amount of N in the processed wastewater stream.

In an embodiment, the wastewater stream comprises a centrate from an anaerobic digestion step of a wastewater treatment plant using a wastewater treatment process. In more detail, the centrate can be produced by subjecting a wastewater stream to an nitrification/dentrification digestion step in a bioreactor, wherein $N_2$, $NO_3$ and $NH_4^+$ are produced; subjecting the sludge of the nitrification/dentrification bioreactor to an anaerobic digestion step; dewatering the effluent of the anaerobic bioreactor creating a centrate and a sludge. The method may also include carrying out the anaerobic digestion step in two stages, where the first stage, consisting of hydrolysis, acidogenesis and acetogenesis is followed by the second methanogenisis stage. In so doing, the hydrolysis, acidogenesis and acetogenesis stage supplies acetate to the organism that produces the arginine-enriched polypeptide, while N in the form of $NH_4^+$ is supplied by the second methanogenic stage of the anaerobic digestion step. The method may include adding a C-source such as acetate, methanol or glycerol to the nitrogen-containing waste stream.

The arginine-enriched polypeptide can include a polypeptide selected from the group consisting of Met-x-$Arg_{5-20}$, $Arg_{5-20}$ and a polypeptide mixture with an average size of between 5 and 20 arginines. The arginine-enriched polypeptide can include a secretory sequence, which is capable of directing secretion outside of a cell. The organism producing the arginine-enriched polypeptide can include a transformed bacterial organism.

The methods may include a step of removing the produced arginine-enriched polypeptide from the wastewater stream which includes flowing the effluent from the culturing step over a cation exchange material under conditions that allow binding of the arginine enriched polypeptide to the cation exchange material, followed by optionally eluting the bound arginine-enriched polypeptide from the material and collecting the eluted arginine-enriched polypeptide.

The method may also include supplying a plant with the produced arginine-enriched polypeptide from the wastewater stream, and the produced arginine-enriched polypeptide increases the growth or production of the plant.

The present invention also includes a method to make an arginine-enriched polypeptide enriched fertilizer by the methods of the invention, and increasing the growth or production of a plant by applying to the plant an arginine-enriched polypeptide enriched fertilizer produced by the methods of the invention.

BRIEF DESCRIPTION OF THE FIGURES

FIG. 6 shows increased germination and biomass yield of *Arabidopsis thaliana* due to the addition of polyarginine or arginine to N-replete growth media.

FIG. 7 shows in table form the inhibition of the binding of cobalt to CM sepharose by polyarginine.

FIG. 8 shows a process diagram for a conventional wastewater treatment plant.

FIG. 9 shows a process diagram for a NAB process.
FIG. 10 shows a process diagram for a NAB process.

DETAILED DESCRIPTION

Figure 1:
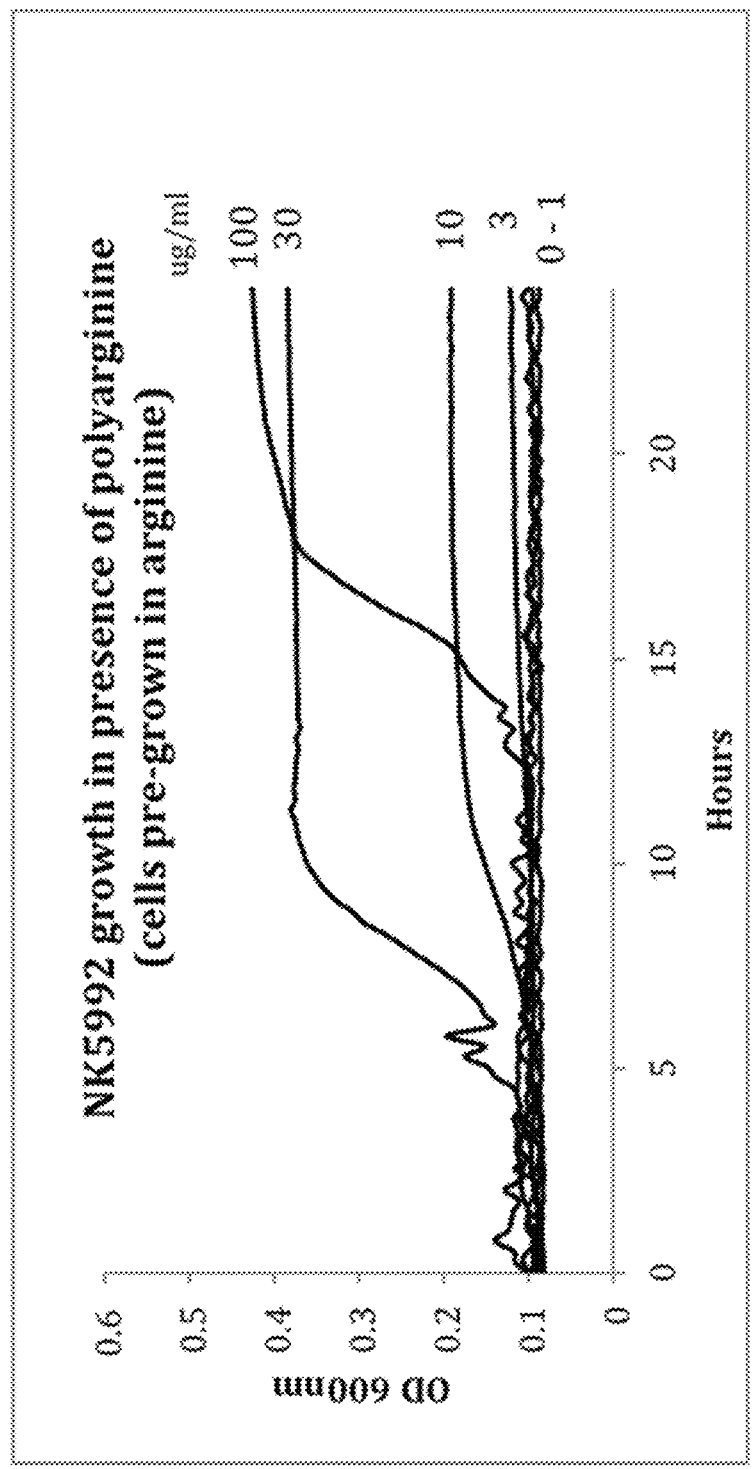
FIG. 1 shows the use of polyarginine for growth by a strain of *E. coli* cells that are auxotrophic for arginine.

While various aspects and features of certain embodiments have been summarized above, the following detailed description illustrates a few embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. Several embodiments are described and claimed herein, and while various features are ascribed to different embodiments, it should be appreciated that the features described with respect to one embodiment may be incorporated with other embodiments as well. By the same token, however, no single feature or features of any described or claimed embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

The present invention, in an embodiment, describes a method, termed NAB (Nitrogen Arginine Biorecovery) to convert, for example, wastewater N to an easily extracted, pure and valuable product, polyarginine. The present invention provides the insight that multiple, highly positive charges on polyarginine act as a handle for efficient separation from wastewater as well as the prior-mentioned attribute for binding soil. For example, cation exchange media, being negatively charged, can be used to pull the polyarginine from the wastewater treatment plant (WVVTP) wastewater stream. Making polyarginine displaces the wastewater energy costs and biosolid disposal costs typically involved in driving N to $N_2$ gas.

The invention, in one embodiment, describes a method for increasing polyarginine production from bacteria. Different approaches to producing, for example, increased arginine levels in organisms, or for increasing peptide or protein levels in bacteria, or for increasing levels of peptide secretion, are generally known in the art and are referenced herein. The methods of the invention also describes a procedure for screening for increased levels of polyarginine production.

The current invention provides the insight that N fertilizer can be designed to actually bind soil (since soil is negatively charged), and that extremely tight binding to soil would cause less pollution, less run off, less volatilization, and timed availability of N to microbes and plants. The present invention specifically uses the amino acid highest in N-arginine- and makes long polymers of arginine that will tightly bind soil for predictable breakdown rates.

Municipalities, agriculture and industry are charged by governments to limit the effluence of N compounds into the environment. The current practice is generally to carry out nitrification/denitrification to reduce influent N load followed by anaerobic digestion to reduce the cell mass that is produced during nitrification/denitrification. In this practice, the N-rich influents are first treated to microbial aerobic oxidation with conversion of ammonia to nitrite and then to nitrate. This is then followed by anoxic microbial treatment with reduction of nitrate to $N_2$ and $NH_3$. Alternately, the anoxic treatment may be followed by the aerobic treatment. In this way fixed N (often sourced from fertilizer) is lost either by disposal of the treatment microbes or by emission of $N_2$ to the air. The above process accounts for some 25% of all wastewater treatment costs due to the energy requirements of oxygenation, and later due to the costs in disposing of the biosolids resulting from cell mass buildup during the nitrification/denitrification phase.

The present invention includes a method for the production of arginine-containing polypeptide from wastewater which is termed the Nitrogen Arginine Biorecovery method (NAB). In one embodiment, the invention includes a method to increase conversion of nitrogen in a nitrogen-containing wastewater stream to an arginine-enriched polypeptide. This method includes the following steps. The method includes supplying a nitrogen-containing wastewater stream; culturing an organism in the waste stream that produces an arginine-enriched polypeptide to produce the arginine-enriched polypeptide; and removing the produced arginine-enriched polypeptide from the wastewater stream to create a processed wastewater stream.

The invention may also include a method to increase conversion of nitrogen in a nitrogen-containing wastewater stream to an arginine-enriched polypeptide. This method may include supplying a nitrogen-containing wastewater stream; culturing an organism in the wastewater stream, wherein the organism is capable of producing an arginine-enriched polypeptide, to produce the arginine-enriched polypeptide; and removing the produced arginine-enriched polypeptide from the wastewater stream to create a processed wastewater stream, wherein the processed wastewater stream has a lower nitrogen content.

FIGS. 8-12 provide process diagrams of a conventional wastewater treatment process in a treatment plant, as well as an overview of Nitrogen Arginine Biorecovery (NAB). In FIGS. 8-10, the solid lines track the flow of N from WWTP N influent to products, the thickness of the line indicates flux. Sizes of boxes indicates which elements of the system are emphasized.

FIG. 8 shows a process diagram for known WWTP processes where N is mostly converted to nitrogen gas in the aerobic basin 31 at large electricity cost ("AB"; here the primary unit and many other steps are omitted for clarity). The cell mass grown in the AB 31 is then reduced in volume during the anaerobic digestion 22 ("AD") phase. The resulting AD sludge resulting from 22 is dewatered 23 forming the final sludge 25 and liquid centrate 26. The centrate 26 is high in $NH_4^+$ (containing about 25% of the influent N) and is redirected back to AB 31. The sludge 25 (7% N by weight) must then be dumped at costs approaching 20% of all wastewater treatment costs.

FIG. 9 shows one embodiment of the overall NAB process as coupled to conventional WWTP systems. $NH_4^+$ in the centrate 26 is converted into the NAB reactor 27 along with added acetate 28 from the Centrate 26 from AD 22 into polyarginine 29. AD 22 is treated as a two-stage reactor where the initial acetogenic stage is utilized as a source of acetate for NAB reactor 27. Since less $NH_4^+$ is returned to the primary WWTP unit (AB 21), less overall N is processed in the primary unit and therefore less $N_2$ gas is emitted and less cell mass is formed, eventually lowering sludge 25 production. NAB cell mass after separation from polyarginine 29 is returned to the AD 22 step for treatment.

FIG. 10 shows another embodiment of the NAB process. Outflow from the AD 22 (Centrate 26) is converted to polyarginine 29 in NAB 7. The NAB 27 and AD 22 reactors are balanced, most N is converted to polyarginine 29 at the expense of sludge 25 production. Not shown is the production of methane gas in the AD unit. It is expected that acetate redirection into polyarginine will decrease methane formation.

Figure 11:
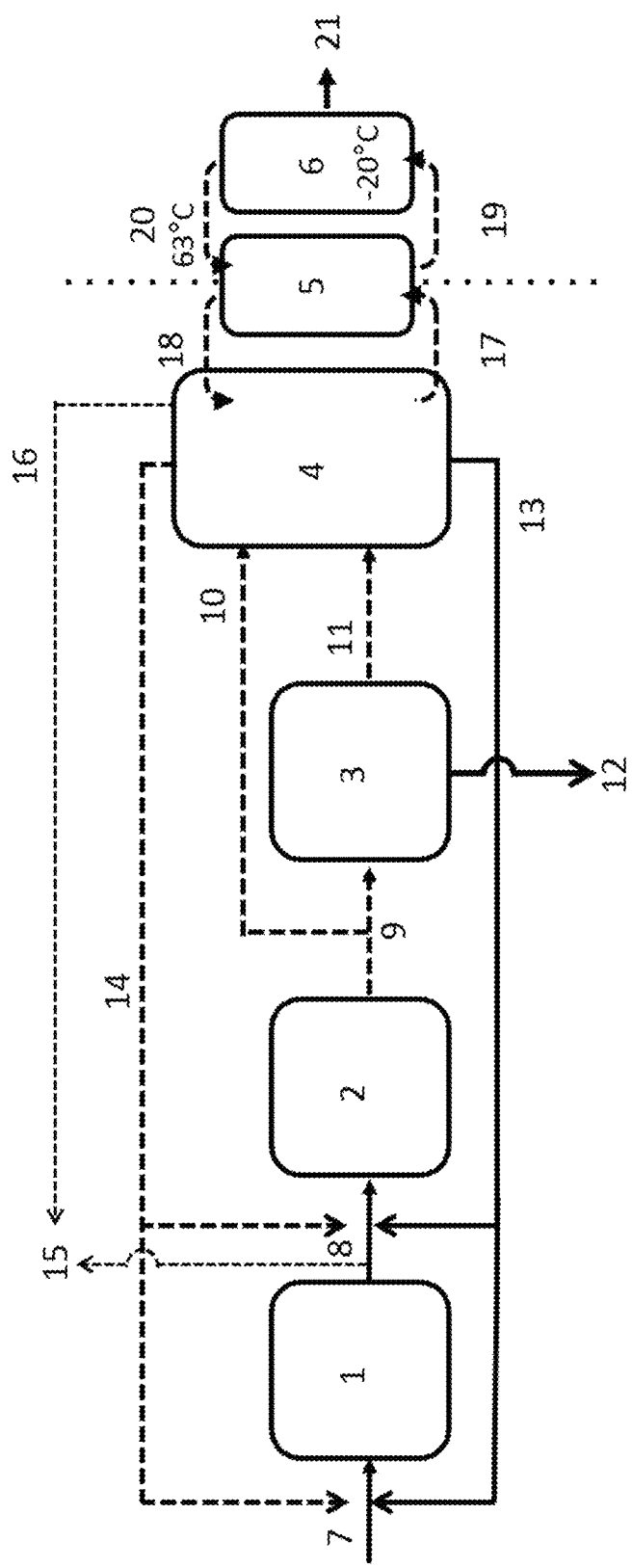
FIG. 11 shows a process diagram for a NAB process.

FIG. 11 shows another embodiment of the NAB process. In this process, influent 7 which can include WWTP influent, NAB cells 13 or NAB effluent portion 14 from NAB reactor 4 enters primary and aerobic basin reactor 1 followed by anaerobic digester acetogenic stage 1 2 followed by stage 2 anaerobic digester 3 which results in a centrate 11 which is then input into NAB reactor 4 to produce polyarginine, which is then captured on cation exchange column 5. Recrystallization tank (batch; −20 C) 6 provides for obtaining polyarginine after removal from cation exchange column 5. Effluent obtained from NAB reactor 4 may be returned to primary and aerobic basin reactors 1, 2, or directed 16 to plant effluent stream 15. Acetate feed 9 is shown optionally input into stage 2 AD 3 and/or acetate feed 10 into NAB reactor. Sludge 12 from AD 3 is waste. Plant effluent 15 is depleted in nitrogen. A portion 17 of NAB effluent is provided to cation exchange column 5 to produce polyarginine 21. Effluent 18 from cation exchange column 5 is returned to NAB reactor 4. Cation exchange column 5 may be stripped of polyarginine 21 using step 19 hot NaOH/methanol and returned to cation exchange 20.

Figure 12:
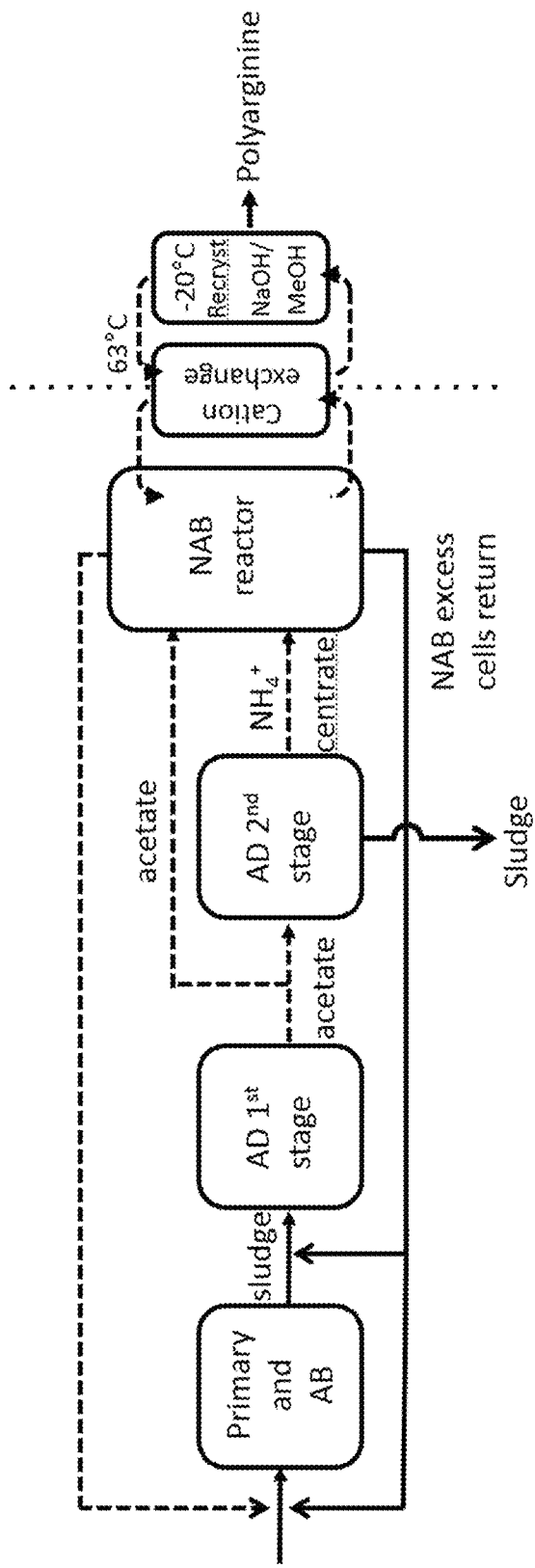
FIG. 12 shows a simplified process diagram for a NAB process.

FIG. 12 shows a simplified version of an NAB process diagram used together with a conventional waste water treatment processes.

In principle, the NAB method could be used with any source of N such as slaughterhouse waste, agricultural waste, industrial waste and municipal waste. parts of the invention described here for municipal waste would also apply to any N-rich wastewater or waste stream and should not be limited to municipal wastewater alone. For instance, a wastewater stream that is high in N, but low in available carbon might be mixed with carbon-rich media for the NAB process. The NAB process may also be applied to entire wastewater streams or to partial streams or partially treated wastewater streams. Because the NAB process actively pulls N from solution, ties the N up as the arginine-enriched polypeptide, and removes the arginine-enriched polypeptide from solution, NAB can reduce nitrogen levels in the waste stream by at least 1%, at least 2%, at least 3%, at least 4%, at least 5%, at least 10%, at least 15%, at least 20%, at least 25%, at least 30%, at least 35%, at least 40%, at least 45%, at least 50%, at least 60%, at least 70%, at least 80% or at least 90%. Alternatively, nitrogen levels in the waste stream may be reduced to below 100 ppm, below 90 ppm, below 80 ppm, below 70 ppm, below 60 ppm, below 50 ppm, below 40 ppm, below 30 ppm, below 20 ppm, below 15 ppm, below 10 ppm, below 9 ppm, below 8 ppm, below 7 ppm, below 6 ppm, below 5 ppm, below 4 ppm, below 3 ppm, below 2 ppm, below 1 ppm, below 0.5 ppm, below 0.1 ppm, below 0.05 ppm, or below 0.01 ppm in wastewater stream effluents prior to release.

In one embodiment, the wastewater stream includes a centrate from a wastewater treatment plant using a wastewater treatment process, and/or wherein the centrate is from an anaerobic digestion step from a wastewater treatment process.

The method includes wherein the wastewater treatment process includes subjecting a wastewater stream to an aerobic digestion step in an aerobic bioreactor, wherein $N_2$ and ammonium are produced; subjecting the effluent of the aerobic bioreactor to an anaerobic digestion step; and dewatering the effluent of the anaerobic bioreactor creating a centrate and a sludge. As known in the art, acetate or another carbon source may be added to the nitrogen-containing waste stream or any effluents of any processes performed on the nitrogen-containing waste streams.

The nitrogen-containing feed stream can include any wastewater feedstream known in the art, and in particular, can include a municipal wastewater feedstream, an agricultural wastewater feedstream, an industrial wastewater feedstream, and/or a holding pond/lagoon feedstream.

In an embodiment, the methods may include the step of removing the produced arginine-enriched polypeptide from the wastewater stream to create a processed wastewater stream. This step includes a step of flowing the effluent from the culturing step over a cation exchange material (CEM) under conditions that allow binding of the arginine enriched polypeptide to the cation exchange material. The method further comprises eluting the bound arginine-enriched polypeptide from the material and collecting the eluted arginine-enriched polypeptide.

In an embodiment, the organism is cultured with pretreatment of the nitrogen containing feedstream using conventional wastewater processes as are known in the art. The method includes subjecting a wastewater stream to an at least partial nitrification/denitrification step, to produce a pretreated effluent; subjecting the pretreated effluent to an anaerobic digestion step to create a treated effluent; and subjecting the treated effluent to conditions, which allow the organism to proliferate and/or express an arginine-enriched polypeptide. The method may include the conventional methods of adding a carbon source or other nutrients by methods known in the art to the wastewater stream.

Conventionally, a wastewater stream may be pretreated in a primary wastewater treatment process, for instance, where wastewater is temporarily held in a tank where heavier solids can settle to the bottom, while any lighter solids and scum float to the surface. The settled and floating materials are desludged or held back and the remaining liquid may be discharged to nitrification/denitrification or partial nitrification/denitrification before use with the NAB process. For the instant invention, one may eliminate or conduct a partial nitrification/denitrification step of the wastewater. Nitrification/denitrification refers to the process of removing nitrogen gas from the wastewater, and includes, for example, adding oxygen and allowing the organisms to consume the added oxygen, in the process producing nitrogen containing compounds, a process that can be repeated.

An important aspect of this present invention is the method of N remediation whereby N is redirected to the production of polyarginine instead of $N_2$ gas. In this aspect, cells draw N-rich compounds from the medium by conversion of the N into a secreted arginine-rich protein, which is itself continuously drawn away from the cells by binding to CEM. In some embodiments, the CEM polyarginine removal step can be in the same reactor in which cells are producing the polyarginine (the main NAB reactor; see example 6) or the CEM can be in a separate column where the feed from the main NAB reactor is cycled over CEM. See FIGS. 4 and 5.

The N-rich feed stream may include waste streams such as municipal, agricultural, and/or industrial wastewater, or water in holding ponds and lagoons, or any defined media with the intent to maximize the production of the arginine-enriched polypeptide. Macronutrients and micronutrients may be added as known in the art to these media to ensure organism survival or productivity. For example a carbon source may be added. Exemplary added carbon sources include methanol or glycerol, or a feed stream that is high in a carbon source. Acetate may be added either by action of the first stage of anaerobic digestion, or by harvesting the carbon produced in the first stage of anaerobic digestion. Wastewater and waste streams may be altered prior to NAB, for instance by being partially purified, or for instance by screening, sedimentation, flocculation, treatment with specific microbes or reactor types.

In some embodiments the CEM, that is loaded with sufficient arginine-enriched polypeptide, is separated from the flow of the main NAB reactor and washed with a wash solution to remove weakly-bound impurities. In some embodiments the wash solution is comprised of a high-pH wash solution of pH 11-12.5 NaOH, but this solution could be any solution found in the art, for instance, solutions containing salt or detergent, or differing bases such as $Ca(OH)_2$, or some combination thereof. In some embodiments, after washing the CEM is then returned to the flow of the main NAB reactor for re-exposure and attachment of more arginine-enriched polypeptide. In this way the polyarginine can compete with less strongly-bound constituents such as heavy metals. In some embodiments the arginine-enriched polypeptide is bound to the CEM at high arginine-enriched polypeptide concentrations so the anionic groups on CEM are saturated with arginine-enriched polypeptide in order to facilitate the final purification of the arginine-enriched polypeptide and to ensure that heavy metals or other positively-charged molecules are not co-captured and purified. In some embodiments the CEM, after washing with the wash solution, is washed and dried with a secondary wash solution. In some embodiments this secondary wash solution is methanol. In some embodiments the wash solution and secondary wash solutions can be recycled for re-use, or can be added back into the wastewater input stream for processing. In some embodiments the CEM is then suitable for direct use, for instance as a nitrogen-containing cationic exchange medium fertilizer.

In some embodiments, the arginine-enriched polypeptide, after binding to the CEM at high concentration, is released from the CEM using a stripping solution to produce arginine-rich proteins for direct use as fertilizer or for further processing for other uses. In other embodiments the arginine-enriched polypeptide is then purified from the stripping solution.

The stripping solution could in practice be any solution inorganic or organic, polar or non-polar, low-salt or high-salt, high-pH or low-pH, high or low temperature, or a combination thereof, such that the polyarginine is stripped from the cationic exchange medium.

In some embodiments, the stripping solution is anhydrous methanol with 200 mM-10M NaOH, but preferably 0.75-2M NaOH, and the solution is held at 35-63 degrees C. for a given time such as 5 minutes such that the high pH and temperature causes the polyarginine to release from the CEM into the stripping solution.

In some embodiments the polyarginine could be purified from the stripping solution through typical methods, for instance recrystallization, evaporation, salting out, trapping on other exchange media, and liquid-liquid extraction.

In one embodiment the polyarginine is purified from 0.75-2M NaOH in anhydrous methanol held at 35-63 degrees C. by dropping the temperature to the point where the polyarginine recrystallizes out. In one embodiment the temperature is dropped to 4 degrees C. and held for 1 hour. In another embodiment the temperature is dropped to −20 degrees C. and held for 30 minutes. In some embodiments the recrystallized polyarginine is washed with a reagent in which polyarginine is not soluble, but that removes the other impurities. In one embodiment the arginine-enriched polypeptide is washed with anhydrous methanol to remove traces of the NaOH used to solubilize the arginine-enriched polypeptide in the methanol. The arginine-enriched polypeptide can then dried to provide pure, optionally solid, and optionally sterile polyarginine.

Example 7 describes the concentration and purification of arginine from solution by saturating onto CEM, washing, stripping and recrystallization at 4 C.

Figure 5:
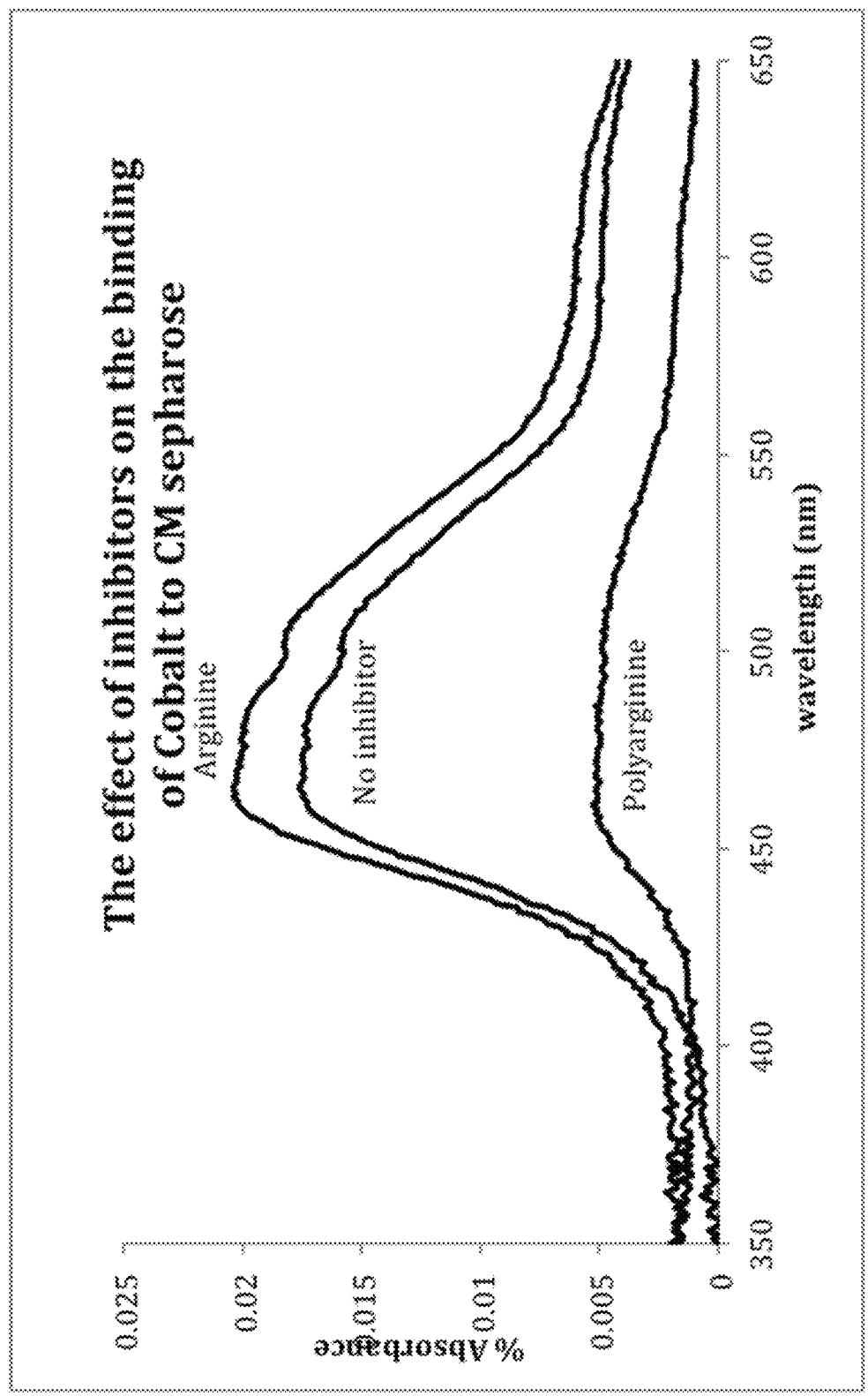
FIG. 5 shows in graph form the inhibition of the binding of cobalt to CM sepharose by polyarginine.
Figure 13:
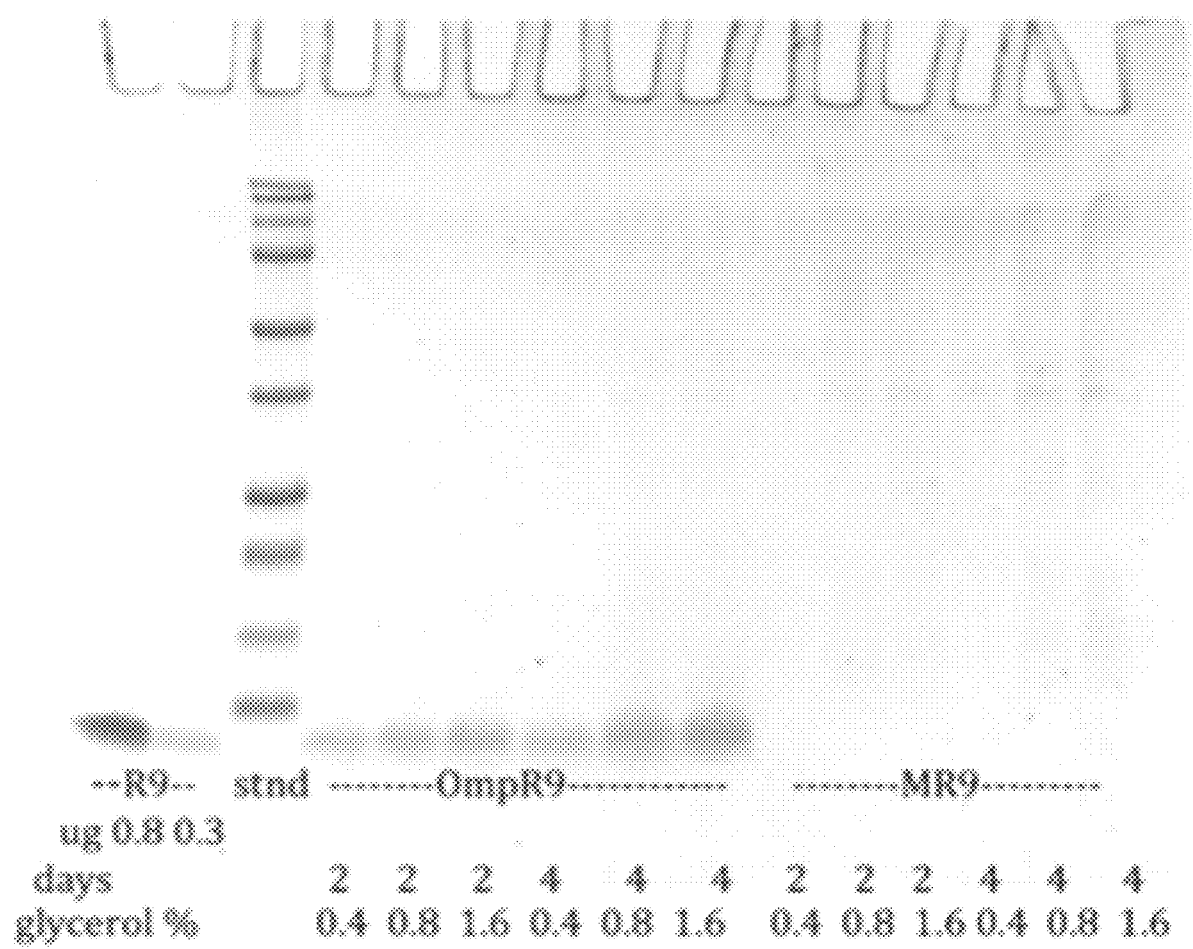
FIG. 13 shows a photograph of a electrophoresis gel showing production of polyarginine by *E. coli* where the polyarginine was continuously isolated from solution using cation exchange media.

A significant aspect of NAB is the preferentially continuous removal of arginine-rich protein from the culture medium using cation exchange in order to drive N recovery. Semi-continuous removal and batch removal of arginine-rich proteins is also a possibility. This aspect of NAB relies on the difference in binding of N as fixed in arginine-rich proteins versus the binding of N in forms found in the feed stream, generally $NH_3$, $NH_4$, $NO_2$ $NO_3$ and forms of organic N such as that found in nucleotides and (non-arginine-rich) proteins. The guanidinium group of arginine is strongly positively charged, having a pKa of approximately 12.4. This group allows binding to cation exchange resin even at basic pH levels and in the presence of competing cations such as metals. Example 5, FIG. 5 and FIG. 7, shows that cobalt is inhibited from binding cation exchange media in the presence of competing polyarginine. Furthermore it is expected that the presence of a multiplicity of arginine residues within an arginine-rich protein will have a multiplicative effect upon binding affinity to cation exchange media, particularly in regards to displacement of other competing non-polycationic cations such as free arginine monomer or metals, and the displacement of less strongly polycationic complexes such as poly(diallyldimethylammonium) chloride, and/or the quaternary ammonium compounds commonly used in soaps, shampoos, and fabric softeners. Therefore this high number of localized positive charges on arginine-rich proteins will facilitate removal of the arginine-rich protein from the culture medium even in the presence of competing, positively charged molecules. Example 2 shows that NAB drives N recovery from media to a much greater extent in the presence of cation exchange media than in its absence, resulting in lower final concentrations of N in growth media when NAB is practiced in the presence of cation exchange media than when practiced in its absence. Example 6, FIG. 13 shows that polyarginine (OmpA-R9) can be pulled directly from cells growing in culture medium in a single step purification using cation exchange media. In one of the embodiments of the invention, modifications to the arginine-rich protein, in particular increases in length of polyarginine regions, drive greater N recovery.

The state of the art production of pure products directly from wastewater is essentially limited to the production of methane, although if the feed stream is pure and fairly high in carbon, there are some instances of producing ethanol. Other known products from wastewater are the production of algal biomass for downstream conversion into biofuels. About 60% of biosolids produced by WWTPs are currently directly returned free to agricultural operations; farmers are generally satisfied with this arrangement. However, biosolids are of unknown and variable pathogen or toxin content, are regulated only for use on certain crops, are not soluble, are problematic to spread during the growing season, and lead to volatilization and run-off, particularly as they sit during winter months. Similar issues are present for such products as Milorganite, which are pelleted, heat-treated biosolids from WWTPs. They are effectively sold at-cost or at a loss in order to defray dumping fees associated with typical biosolids. While not pathogenic, these compounds are known to contain heavy metals and other toxins. Finally, certain wastewater operations, such as protein and peptide concentrates from slaughterhouses or the use of manure either directly or having been treated are considered options. However, these preparations are either insoluble, potentially pathogenic or inconsistent or unstable by nature.

In contrast, polyarginine is likely to be free from potential toxins and pathogens due to the CEM purification step. There is no prior art for the production of arginine-enriched polypeptides from wastewater.

An important aspect of this invention is the NAB organism whereby arginine-rich proteins are directed into the culture media either in an active or passive manner. NAB uses organisms optimized at a number of discrete steps where the entirety of these steps is directed at increasing the amount of N trapped as arginine-rich protein. NAB criteria for organisms comprises: increased N uptake; increased production of arginine; decreased catabolism of arginine; increased production of arginine tRNAs; increased production of arginine-rich proteins; decreased production of competing products; increased secretion of arginine-rich proteins; and, specifically trapping the arginine-rich protein on cation exchange media.

Individually, a number of the steps described for NAB organisms have been applied by the art to the production of arginine monomers. By way of example: down-regulation of the arginase, arginine decarboxylase, arginine deiminase, arginine amidinotransferase, arginine succinyltransferase and arginine oxidase/dehydrogenase pathways. All of these modifications were made to increase the production of arginine monomer as a product. The current invention incorporates some of these steps, but only does so in treating arginine monomer as a transient compound that is immediately converted into an arginine-rich, secreted protein. The previous art has not coupled over-production of arginine to the subsequent over-production of arginine-rich proteins. In one embodiment, argO export genes are mutated to reduce export of arginine monomer from the cell. This leads to an increased production of arginine-rich proteins. This is in direct opposition to the approach taken by the art where arginine export is increased in order to increase the production of arginine monomer. Also, the invention contemplates knocking out carboxypeptidase B gene in order to lower degradation of arginine-rich proteins and thereby increase product yield in the current invention. This would be expected to have a neutral or negative effect in the case where production of arginine monomer is preferred.

In an embodiment, a step in NAB is the production of arginine-rich proteins that are efficiently transported across the cell membrane or cell wall and outside into the surrounding medium. Prior art has shown that $R_9$ is readily taken up by cells. We show in Example 2 that production of Met-$Arg_9$ peptide, when produced by E. coli is implicated in reduction of ammonium concentration in growth medium using the NAB process. According to the invention, % arginine of the produced peptide, and/or length of the arginine-rich peptides can be modified to promote flux of the arginine-rich protein across the cell wall and out into the surrounding medium. Similarly according to the invention, peptides may be actively secreted into the exterior medium by the addition of secretion coding sequences; this is a distinctly different method of transport than that which the arginine monomer undergoes in prior art. Example 6 shows R9 secretion using an OmpA secretory system.

The arginine-enriched proteins may include secretory sequences that act to direct the arginine-enriched protein to secretion by the cell. Such secretory signals may be cleaved off in the process of secretion, cleaved off after production, or left on the arginine-rich protein.

The organisms may be isolated from various wastewater sources or from agricultural lagoons. Multiple different types of organisms may be utilized, either singularly or in combinations in order to efficiently convert a given feedstock to arginine-rich protein. Example organisms include facultative bacteria, anaerobic bacteria, aerobic bacteria, such as nitrifying bacteria, exemplified by genus *Nitrosomonas* and *Nitrobacter*, sulfur bacteria, exemplified by genus *Thiothrix* and *Thiobacillus*, and iron bacteria, exemplified by genus *Siderocapsa*. Other candidate organisms include those typically used for the production of arginine (example genus *Corynebacterium* (*Brevibacterium*), *Bacillus*, and *Serratia*). Other candidate organisms include acetogenic bacteria (example genus *Acetobacter*), coliforms (example genus *Escherichia*), cyanobacteria (example genus *Oscillatoria*), fecal coliforms, fermentative bacteria (example genus *Proteus*), filamentous bacteria (example genus *Haliscomenobacter*), floc-forming bacteria (example *Zoogloea*), gliding bacteria (example genus *Beggiatoa*), gram-positive bacteria (example genus *Bacillus*), gram-negative aerobic cocci and rods (example genus *Acetobacter*), gram-negative facultative anaerobic rods (example genus *Escherichia*), hydrolytic bacteria (example genus *Bacteriodes*), methane-forming bacteria (example genus *Methanobacterium*), nocardioforms (example genus *Nocardia*), pathogenic bacteria (example genus *Campylobacter*) poly-P bacteria (example genus *Acinobacter*), saprophytic bacteria (example genus *Micrococcus*), sheathed bacteria (example genus *Sphaerotilus*), spirochetes (example genus *Spirochaeta*), among others.

The organisms can be genetically modified or otherwise selected, for instance by using CRISPR, or for instance using gene drive, to increase the production of arginine-rich proteins through down-regulation of arginine export genes such as argO, through down-regulation of genes that would degrade arginine-rich proteins, such as carboypeptidase B, and through limiting or eliminating the production of arginine-rich by-products such as cyanophycin that would otherwise compete with production of the arginine-rich protein. Included are modified organisms containing combinations of these modified attributes.

The arginine-rich proteins may be derived from endogenous genes in either the NAB organism itself, or other organisms that have sufficiently large arginine-rich tracts. For instance, 12 native E. coli proteins that have tracts of polyarginine that might be used as templates for native arginine-rich proteins, e.g., hypothetical protein WP_077727669.1; sequence RRRRRRRRKR (SEQ ID NO: 1); hypothetical protein WP_102778346.1, sequence RRRRRRRHRR (SEQ ID NO: 2); hypothetical protein B1739_27650 OOV66526.1, sequence RRRRRRKKRKKGRRRR (SEQ ID NO: 3); glucans biosynthesis glucosyltransferase MdoH, WP_097764455.1, sequence RRRRRRRR (SEQ ID NO: 4); glucan biosynthesis glucosyltransferase HODH35595.1, sequence RRRRRRRR (SEQ ID NO: 5); hypothetical protein, WP_085034537.1, sequence RRRRRRRKR (SEQ ID NO: 6); hypothetical protein B1739_20765 OOV67953.1, sequence RRRRRKRRR (SEQ ID NO: 7); collagen triple helix repeat family protein EHW28218.1, sequence RRRRRQRRR (SEQ ID NO: 8); Putative cation-transporting P-type ATPase CDL58153.1, sequence RQRRRRRRR (SEQ ID NO: 9); tail fiber protein, partial, EIL06711.1, sequence RRRRRMPERRRR (SEQ ID NO: 10); flagellar biosynthesis protein EKH62751.1, sequence RRRRRRKR (SEQ ID NO: 11); polynucleotide adenylyltransferase WP_089638282.1; sequence RRRHRRPRRR (SEQ ID NO: 12).

The arginine-rich proteins may be selected from currently secreted native arginine-rich proteins that are isolated from solutions in which the NAB organism is grown by adding CEM to the growing culture, washing the CEM at high pH, and collecting the remaining proteins for peptide analysis.

The organisms may also be genetically modified or otherwise selected, for instance by using CRISPR, or for instance using gene drive, to specifically increase for arginine-rich protein production: by way of example, through up-regulation of the arginine-rich protein itself; through up-regulation of levels of arginine tRNAs; through down-regulation of other arginine-rich proteins. Included are modified organisms containing combinations of these modified attributes.

The organisms may also be genetically modified or otherwise selected, for instance by using CRISPR, or for instance using gene drive, to specifically increase for arginine-rich protein production: by way of example, up-regulation of arginine synthesis genes such as argininosuccinate lyase, down-regulation of arginine catabolism genes such as arginase, and down-regulation of arginine synthesis feedback inhibition genes such as argA. Included are modified organisms containing combinations of these modified attributes.

The organisms producing the arginine-rich proteins can be N-fixing organisms, such as, for example, cyanobacteria or other photosynthetic organisms such as non-sulfur purple bacteria or a mixture of N-fixing organisms and possibly complex mixtures of other organisms so as to facilitate the production of arginine-rich proteins. Optionally, the N-fixing organisms are genetically modified or otherwise selected to increase the level of N fixation.

An important aspect of this invention is the screening of organisms that efficiently secrete arginine-rich proteins, or screening for arginine-rich proteins that are efficiently secreted by organisms. As is known in the art, Coomassie Brilliant Blue G-250 is used to detect arginine levels; similarly Sakaguchi reagent is used to detect arginine; such dyes could be adapted for use in an agar detection system to distinguish colonies of cells having higher rates of polyarginine production and secretion. Similarly, other acid dyes, that by nature will bind tightly to the positively-charged guanidinium groups on polyargine may selectively change their color when bound by arginine-rich protein and thus serve as a reporter system for screening for arginine-rich protein secretion by organisms. Similarly an antibody or aptamer for detection of arginine-rich proteins could be used to screen for arginine-rich protein production. This invention discloses that *Escherichia coli* strain NK5992, an arginine auxotroph, grows on polyarginine, and therefore can be used as a sensor strain to detect increased polyarginine production and secretion by the production strain, see FIG. 9 and Example 8.

The arginine-rich proteins may be produced by an organism or a transformed organism. Such organisms may be grown photoautotrophically, chemoautotrophically or heterotrophically on a N-rich feedstream in such a way so as to stimulate N uptake and increase production of arginine-rich proteins.

The methods of the invention also include a method to make a composition that includes an arginine-enriched polypeptide enriched fertilizer. This method includes supplying a nitrogen-containing wastewater stream; culturing an organism in the waste stream that produces an arginine-enriched polypeptide to produce the arginine-enriched polypeptide; flowing the effluent from the culturing step over a cation exchange material under conditions that allow binding of the arginine enriched polypeptide to the cation exchange material; and eluting the bound arginine-enriched polypeptide from the material and collecting the eluted arginine-enriched polypeptide to form the arginine-enriched polypeptide enriched fertilizer.

In one embodiment, the eluted arginine enriched polypeptide is bound to a cation exchange material, which can include peat, diatomaceous earth, compost, clay, soil, and/or commercially available cation exchange media, and/or combinations thereof to form the arginine-enriched polypeptide enriched fertilizer.

In an embodiment, the present invention also includes methods to increase the growth or production of a plant which includes supplying a nitrogen-containing wastewater stream; culturing an organism in the waste stream that produces an arginine-enriched polypeptide to produce the arginine-enriched polypeptide; flowing the effluent from the culturing step over a cation exchange material under conditions that allow binding of the arginine enriched polypeptide to the cation exchange material; eluting the bound arginine-enriched polypeptide from the material and collecting the eluted arginine-enriched polypeptide; and applying at least a portion of the arginine-enriched polypeptide to a plant in a growth phase or a production phase.

Herein by definition the term "protein" refers also to the terms "peptide" and "polypeptide", and the term "polyarginine" specifies an arginine-rich protein, or a region within a protein, consisting entirely of arginine without other amino acid residues, where the terms "$R_n$" and "$Arg_n$" are polyarginine regions where R or Arg are shorthand for arginine and $n$ is the number of consecutive residues of arginine in the molecule. By Arginine we generally refer to L-Arginine, the form of arginine most commonly found in nature, however, the synthesized version of polyarginine may contain, by definition D-Arginine, or mixtures of the two types. By definition the term "N" refers to nitrogen, the term "CEM" refers to cation exchange material, the term "NAB" refers to nitrogen arginine biorecovery".

An arginine-enriched polypeptide includes a polypeptide with a majority of arginine amino acids. The importance of maximizing the number of arginine amino acid residues is that: 1) the guanidinium group on the arginine has a pKa of approximately 12.4, and increasing the number of arginine amino acid residues increases the Gibbs Free Energy of binding of the molecule to CEM and to soils as the approximate additive of each additional residue; and, 2) that each additional arginine residue contains 4 N, as opposed to most amino acids having only 1 or 2 N. The arginine-enriched polypeptide may have a number of non-arginine modifications which add to the main functionality of the arginine-enriched polypeptide, specifically delaying or enhancing delivery of arginine to soils and plants.

The arginine-rich proteins can be made synthetically but are preferably made by microorganisms.

An arginine-enriched polypeptide of the present invention includes, for example, $Arg_{5-20}$, or $Met-Arg_{5-20}$, or $Met-x-Arg_{5-20}$, or $Met(-Arg_{5-20}-x)_y$, or $sig-Arg_{5-20}$, or $Met-sig-Arg_{5-20}$, or $Met-Sig-(-Arg_{5-20}-x)_z$, or $Sig-(-Arg_{5-20}-x)_z$. $Arg_{5-20}$ or $Met-Arg_{5-20}$, $Met-x-Arg_{5-20}$, or $Met(-Arg_{5-20}-x)_y$, or $sig-Arg_{5-20}$, or $Met-sig-Arg_{5-20}$, or $Met-Sig-(-Arg_{5-20}-x)_z$, or $Sig-(-Arg_{5-20}-x)_z$ and a polypeptide mixture with an average size of between 5 and 20 arginines. However the arginine-enriched polypeptide of the present invention may be between 2 and 400 amino acids in length, between about 4 and about 200 amino acids in length, between about 6 and about 100 amino acids in length, between about 10 and about 50 amino acids in length. An arginine-enriched polypeptide may have an average size of about 2, 3, 4, 5, 6, 7, 8, 9, 10, 11, 12, 13, 14, 15, 16, 17, 18, 19, and 20 arginines in length, but may be longer, such as about 25, 30, 35, 40, 45, 50, 60, 70, 80, 90, 100, 120, 140, 160, 180, 200, 300, 350, or 400 arginines in length.

The arginine-enriched polypeptide of the present invention includes a "$Arg_{5-20}$" region which indicates an average size of between 5 and 20 arginines. The arginine-enriched polypeptide of the present invention includes a section "Met" which refers to the initial amino acid that start many proteins in cells, when absent the Met and other amino acids may have been cleaved off. The arginine-enriched polypeptide of the present invention includes a section "x" which refers to amino acids other than arginine that may be used, for instance, to separate one region of arginine amino acid residues from another. The arginine-enriched polypeptide of the present invention also includes peptides with multiple interrupted arginine sections, $Met-x(-Arg_{5-20}-x)_z$. Where "z" refers to the number of repetitions, typically z is between 1 and 50. The purpose of such repetition being to change the delivery pattern of N upon enzyme degradation in soils or other media, while making one continuous protein.

In some embodiments the arginine-enriched polypeptide includes a section "sig" where sig refers to an optional region that supplies the peptide a secretion signal for secretion from the microorganism. The sig region may or may not be cleaved in the final product. Sig is typically on the N-terminal end of the arginine-enriched polypeptide. For instance $Sig-Arg_{5-20}$.

The arginine-enriched polypeptide of the present invention includes peptides made by non-ribosomal means, such as by enzyme-driven polymerization of arginine amino acid residues. Hence, the polyarginine region may be of indeterminate length, and may represent a pool of different polyarginine lengths.

The arginine-enriched polypeptide of the present invention may include amino acids on the carboxy terminus of the polypeptide that are not arginines.

The arginine-enriched polypeptide of the present invention also includes peptides having modified, or capped amino and/or carboxy termini in order to protect the peptide from degradation and give a delayed N fertilization response.

The arginine-enriched polypeptide of the present invention may be mixed and pooled with other arginine-enriched polypeptides in order to create a variable envelope of N release, for instance; very short arginine-enriched polypeptide may be mixed with very long arginine-enriched polypeptides to create an initial availability of N followed by slower release.

The arginine-enriched polypeptide of the present invention may include other non-arginine-enriched amino acid regions that act in specific ways. In some embodiments this includes antibacterial peptides, antiviral peptides, antifungal peptides, antiparasitic peptides, anti-protist peptides, insecticidal peptides, or protease inhibitors. Some embodiments of antimicrobial peptides include Dermaseptin, Abaecin, Ct-Andropin, Apidaecin IA, and Bactenecin.

The arginine-enriched polypeptide of the present invention may include other non-arginine-enriched amino acid regions that act to direct uptake of the arginine-enriched polypeptide into specific areas of plants. In some embodiments this directed uptake includes into: root cells, stem cells or leaf cells, parenchyma cells, collenchyma cells, sclerenchyma cells; or into xylem, and phloem; or into structures or organelles such as or stomata, cell walls, chloroplasts, cytoplasm, cytoskeleton, endoplasmic reticulum, Golgi complex, microtubules, mitochondria, nucleus, peroxisomes, or plasmodesmata.

The arginine-enriched polypeptide of the present invention may include regions that are specifically used for recognition and uptake by plants that have been engineered to uptake the arginine-enriched polypeptide, including the arginine-enriched polypeptide region itself.

The arginine-enriched polypeptide of the present invention may include formulations containing peptidase inhibitors such as SQ 14,225 that would act to delay soil microbial degradation of the arginine-enriched polypeptide.

The arginine-enriched polypeptide of the present invention may include formulations that help with delivery, including but not limited to waxes, emollients, wetting agents, prilling agents and preservatives such as may be typical in the known art of fertilizer delivery.

Figure 2:
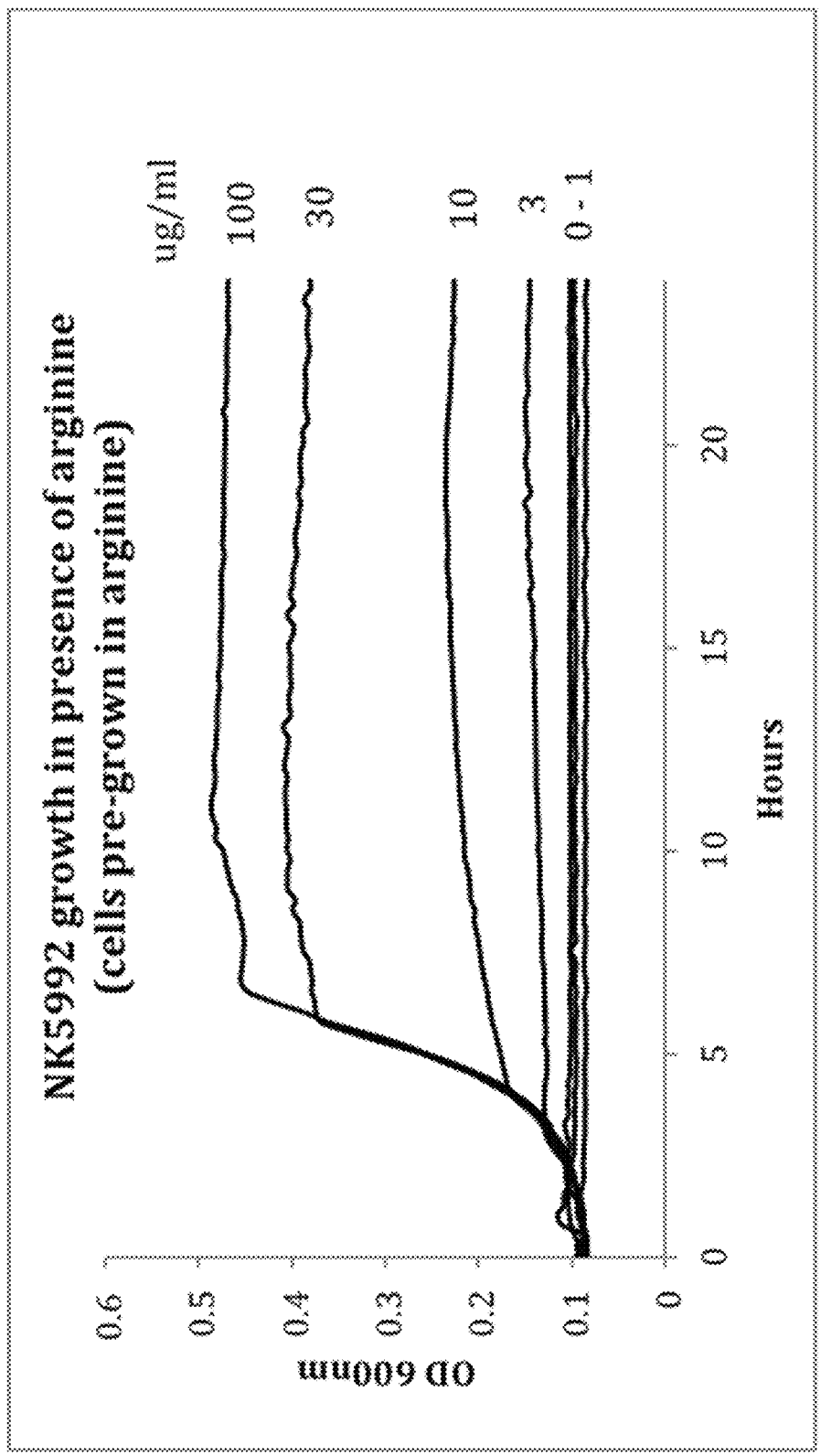
FIG. 2 shows the use of arginine for growth by the same strain of *E. coli* used in FIG. 1.

Polyarginine is approximately 35% N. By comparison $NH_4NO_3$ is 33% N, cyanophycin is 23% and urea is 46%. It is known that the arginine monomer acts as an effective fertilizer, with soil microorganisms readily reducing arginine to produce ammonia, which is then available for uptake by plants. Incorporation of arginine into preferred compounds containing polyarginine-rich regions creates a compound with unique attributes compared to that of arginine alone. For example, as shown in FIG. 1 and FIG. 2, *E. coli* cells can utilize arginine more quickly for growth than they do polyarginine. This lag period suggests that polyarginine acts as a "slow-release" form of arginine. As a second example (FIG. 5) polyarginine inhibits cobalt from binding cation exchange medium whereas arginine alone does not, indicating that the multiplicity of guanidinium groups on polyarginine will bind the cation exchange medium more tightly than arginine alone, facilitating continuous purification and concentration away from competing cations in solution. This also suggests that polyarginine will bind soil more tightly than arginine alone, facilitating slow-release of N. This is the basis for the Nitrogen Arginine Biorecovery method for driving nitrogen recovery into a trapped product, thereby reducing the presence of arginine monomer within the cell so that it is no longer available for feedback inhibition or for conversion into other cellular metabolites such as cyanophycin. The following examples also show ways in which arginine-rich proteins are different than merely adding arginine monomers alone: 1) the length of the polyarginine compound can be manipulated to modify N release rate of the fertilizer in comparison to the monomer arginine alone; 2) arginine monomers do not bind cation exchange media as tightly as polyarginine, this allows facilitated pull-down and purification of the polyarginine; and, 3) polyarginine-rich proteins can include non-basic amino acid residues in order to inhibit certain exoproteases and thereby slow N release rates of the fertilizer.

In Example 1 it is shown that *E. coli* strain NK5992 that normally requires arginine for growth because of a mutation in ArgA, N-acetylglutamate synthetase, does grow on polyarginine. On a per-monomer equivalency, the organism grows more poorly on polyarginine than when fed arginine monomer directly. This indicates that arginine and polyarginine have different modes and rates of uptake and use by this organism. Similarly, there should be different modes and rates of uptake and use of arginine versus polyarginine by soil organisms, including bacteria and plants.

A significant aspect of this invention is that arginine-rich proteins may inherently show slow-release characteristics in terms of supplying nitrogen to plants, since the monomer arginine must be released from polyarginine in a sequential fashion by enzymes prior to incorporation of the monomer into plant or microbial proteins. In this way, the length of the arginine-rich protein, or a mixture of arginine-rich proteins of different lengths is optimized to promote specific nitrogen release rates. According to the invention, soil microorganism uptake rate of polyarginine is related to the length of the polyarginine compound, with longer polyarginine regions leading to slower arginine uptake. By extension, longer polyarginine compounds represent a fertilizer with a slower release rate of nitrogen, and slow release fertilizers can comprise polyarginine compounds of differing lengths.

According to the invention, microorganism uptake rates of polyarginine can be modified by substituting non-basic amino acids in the polymer. By extension such compounds represent a fertilizer with altered nitrogen release rates; slow release fertilizers can comprise polyarginine compounds of different degrees of amino acid substitution.

Arginine-enriched polypeptides of the invention include synthesized arginine-rich compounds comprised principally of L- and/or D-stereoisomers of primarily arginine monomers, but with addition of additional monomers or cross-linkers in order to enable formulation or to alter formulation uptake rates, wherein such compounds are used directly as fertilizer or are first bound to exchange media that is suitable for use as a fertilizer.

This invention therefore describes a method whereby N is in effect continuously pulled from solution by an organism, concentrated into a soluble polymer, secreted, and then collected from solution by soil-amenable cation exchange media so as to drive the flux of N from the feed stream into a concentrated, usable fertilizer or arginine-rich product.

The methods of the invention, in an embodiment, may result in decreasing conventional wastewater treatment electricity requirements by 1%, 2%, 3%, 4%, 5%, 6%, 7%, 8%, 9%, 10%, 11%, 12%, 13%, 14%, 15%, or 20%. The amounts of and/or costs of costs of biosolid disposal by 1%, 2%, 3%, 4%, 5%, 6%, 7%, 8%, 9%, 10%, 11%, 12%, 13%, 14%, 15%, or 20% while decreasing the entire equipment operations of a WWTP by 3%.

In one embodiment, the arginine-enriched polypeptides are trapped and concentrated using cationic exchange media, for example, using either the weak cation exchange material CM sepharose or the strong cation exchange material Sepharose SP.

In one embodiment, the arginine-enriched polypeptides are trapped and concentrated using cationic exchange media (or material) that is suitable for use as a fertilizer, preferably an inexpensive and widely-available material such as peat, diatomaceous earth, clay, soil, or compost, where the added arginine-rich proteins will act as an added growth stimulant.

In one embodiment, the cell production of the arginine-rich proteins is concurrent with trapping the arginine-rich proteins on the cationic exchange media (or material) so as to create a nitrogen recovery method (NAB) where the cation exchange media acts as an ultimate sink for N and thereby drives the cellular uptake of N, conversion into arginine, incorporation into arginine-rich protein, and secretion of the arginine-rich protein.

Accordingly, the instant invention includes a method to increase the growth or production of a plant, comprising supplying the plant with an arginine-enriched polypeptide. The present invention also includes a method to make a composition comprising a nitrogen-containing fertilizer, comprising supplying an arginine-enriched polypeptide; and binding the arginine-enriched polypeptide to a cation exchange material to create the nitrogen-containing fertilizer. The present invention also includes a method to make a nitrogen-containing fertilizer, comprising; culturing an organism which expresses and secretes into the media an arginine-enriched polypeptide selected from the group consisting of Met-x-Arg5-20, Arg5-20 and a polypeptide mixture with an average size of between 5 and 20 arginines; exposing the cultured media or conditioned media to a material that is capable of binding cations under conditions that allow the arginine-enriched polypeptide to bind to the material, wherein the material is selected from the group consisting of peat, diatomaceous earth, compost, clay, or soil to create the composition comprising a nitrogen-containing fertilizer.

The present invention also includes a method to increase the growth or production of a plant comprising: culturing an organism which expresses and secretes into the media an arginine-enriched polypeptide. In one embodiment, the arginine-enriched polypeptide is selected from the group consisting of Met-x-Arg$_{5-20}$, Arg$_{5-20}$ and a polypeptide mixture with an average size of between 5 and 20 arginines. The method also includes exposing the cultured media or conditioned media to a material that is capable of binding cations under conditions that allow the arginine-enriched polypeptide to bind to the material, wherein the material is selected from the group consisting of peat, diatomaceous earth, compost, clay, or soil to create the composition comprising a nitrogen-containing fertilizer; and exposing the plant to the composition comprising the nitrogen-containing fertilizer, wherein the growth or production of the plant is increased.

The present invention also includes a composition comprising a fertilizer which includes a material capable of binding to cations and an arginine-enriched polypeptide.

Another important aspect of this invention is to use cation exchange media such as peat, humus, composted crop residue or diatomaceous earth that are amenable to crop growth. This would allow direct use of the arginine-rich protein-bound cation exchange media as a nitrogen-enhanced fertilizer, making the arginine-rich protein available for conversion to ammonia by soil microbes or direct assimilation of the arginine-rich protein into plant roots. According to the invention, peat and alternatively diatomaceous earth, when bound with arginine-rich protein, supplies nitrogen to soil microorganisms and plants.

Another aspect of the invention is that the arginine-rich protein may instead be removed from the cation exchange medium where the arginine-rich protein is further collected for use in a concentrated form. Therefore, concentrated arginine-rich protein collected from cation exchange medium is directly taken up as a nitrogen source by soil microorganisms and plants.

Another aspect of this invention is that arginine-rich proteins may have specific utility as a foliar application of fertilizer or for direct absorption by plant root cells. It is known that various peptides easily cross the outer cell membrane of a number of known cell types. Such peptides include the TAT peptide, and the polypeptide Arg$_9$, where such peptides have been used to chaperone DNA and/or GFP into barley leaves, tobacco cells, and onion and tomato root cells. There is some indication that arginine-rich proteins taken up by cells either remain inside the cell or are freely diffusible back across the cell wall. There is no prior indication that the TAT peptide, or the polypeptide Arg$_9$ will act as a nitrogen source upon application to soils or directly to plants and that these peptides can support plant growth.

The fertilizer compositions of the present invention disclosed here may be used as a composition containing the arginine-rich protein alone or mixed in as a further composition with other macronutrients and macronutrients required for plant growth, as well as other components that aid in composition delivery, such as surfactants, waxes and emulsifiers.

The disclosed fertilizer compositions of the invention can be supplied as concentrate or ready-to-use liquids, thickened liquids, liquids having components to increase adherence of the disclosed fertilizer to plant surfaces, gels, powders, granules, pellets, blocks, or tablets. A concentrate composition refers to a product that is diluted with water before being applied to the crops. A ready-to-use composition refers to a product that is applied to a crop without dilution. When provided as a liquid, thickened liquid, or gel, the composition can be a concentrate that is diluted with water before being applied to the crop. This allows for less product to be shipped and stored. The product can also be provided as a ready-to-use liquid. When provided as a solid, especially a powder, granule, or pellet, the solid can be applied as a ready-to-use product where the product is scattered around the crops. The product can also be provided as a solid concentrate that is diluted with water before being applied to the crop. In some embodiments, the composition is a ready-to-use liquid. In some embodiments, the disclosed composition is provided as a two-part composition. In some embodiments, the disclosed composition is provided as a one-part composition.

The disclosed compositions of the invention may be provided as a concentrate that is diluted with water to form a ready-to-use composition, or may be provided as a ready-to-use composition. The disclosed compositions may be applied to a seed or plant by scattering, sprinkling, spraying, misting, foaming, dusting, injecting, or applying with a targeted application such as a seed application. As an example, the ready-to-use composition may be a solid that is scattered around a plant or may be a liquid that is applied around or on a plant.

In some embodiments, in one embodiment the compositions of the invention are applied to the seed during planting. This allows the plant to obtain the most benefit from the compositions of the invention, and develop the strongest root system. This will then allow the developed plant to access more water and nutrients which in turn makes it more drought resistant.

In some embodiments, when applying the compositions of the invention to the seeds, the composition may be applied at a given distance from the seed and distance into the soil. In other embodiments, the compositions may be applied to either side of the seed, in front or in back of the seed in the row, or even on the seed. In some embodiments, it may be desirable to not apply the compositions directly to the seed. It may be desirable for the compositions to be applied at the same soil depth of the seed versus above the seed on top of the dirt. When applying the composition with seed planting, the composition may be applied at a concentration or rate of application that is suitable for the specific plant type to be grown, which can be determined by one of skill in the art. In some embodiments, the compositions of the invention are applied or re-applied to the plant leaves.

In some embodiments, it may be desirable for the compositions of the invention to be applied to the seed prior to planting. Optionally this is accomplished as a seed coating or covering.

It may be desirable to foliar-apply the compositions of the invention. This may be a single application, may be part of a series of foliar applications, or may be done in conjunction with an earlier seed application. When applying the compositions of the invention to the leaves, the composition may be applied at a concentration or rate of application that is suitable for the specific plant type to be grown, as can be determined by one of skill in the art.

The present invention also includes a method to enhance germination of a seed, as discussed elsewhere herein. As shown in example 4, FIG. 6, polyarginine and arginine stimulate the germination and growth of *Arabidopsis thaliana* in liquid culture in a dose-dependent manner over the control when added as an extra ingredient to an otherwise complete nitrogen-containing commercial plant tissue culture medium. The invention includes the use of specific amounts of either polyarginine or arginine to obtain increased growth and/or germination of many plant seed types, including, but not limited to all grains, legumes, fruits, flowers, podded vegetables, bulb and stem vegetables, sugar cane, soybeans, maize, rice, wheat, potatoes, sugar beet, cassava, soybeans, tomatoes barley, sweet potatoes, watermelons, bananas, onions, apples, cabbages, oranges grapes, cucumbers, sorghum, cotton, and rapeseed. Also included are application of polyarginine or arginine to other plants including: grains, legumes, fruits, flowers, podded vegetables, bulb and stem vegetables, root and tuberous vegetables, sea vegetables, leafy and salad vegetables, woody species, ornamentals, houseplants, algae and cyanobacteria and plants used for biomass or biofuel production. Arginine and/or polyarginine may be used to increase growth and/or germination of seeds or plant tissue grafts in either liquid culture, hydroponic media, soil, or other media. The invention includes the use of specific amounts of either polyarginine or arginine to obtain increased growth and/or germination of seeds in soil, particularly through the use of direct application or by coating seeds with a specific amount of polyarginine or arginine prior to planting, with amounts of arginine/polyarginine to be used as determined by one of skill in the art. For example, in liquid media, the amount of arginine and/or polyarginine to use can include a range of between about 10 µg/ml and about 1 mg/ml, between about 1 µg/ml and about 800 µg/ml, between about 10 µg/ml and about 500 µg/ml, between about 30 µg/ml and about 300 µg/ml, between about 50 µg/ml and about 150 µg/ml M, or between about 80 µg/ml and about 120 µg/ml, or about 100 µg/ml. Appropriate amounts of arginine/poly arginine to be used in other media types can be determined by one of skill in the art.

The present invention includes the use of specific amounts of either polyarginine or arginine to obtain increased growth and/or germination of seeds in soil, in one embodiment, through the use of direct application or by coating seeds with a specific amount of polyarginine or arginine prior to planting. The present invention provides an embodiment where $R_9$ and other arginine-rich proteins of the invention, applied either as a foliar feed or as a soil nutrient supplies nitrogen to encourage growth of plants.

In another embodiment of the present invention, polyarginine and/or arginine may be used to increase growth amount or growth rate, and/or increase and/or enhance germination of seeds, grafts and/or plant cell culture, including *Arabidopsis thaliana* seeds. Specifically, polyarginine or arginine caused increased plant length, decreased germination time, increased germination percent, and increased total biomass accumulation at the measured stages of plant growth in a dose-dependent manner over a control where polyarginine or arginine was not used.

This invention also recognizes that such concentrated forms of arginine-rich protein has a number of important industrial other than use in fertilizer. By way of example, the production of animal feed, or the production of $Arg_9$ or other arginine-rich proteins of the invention as drug delivery agents. By way of another example, polyarginine may be used as an anionic exchange media, either alone or having chemical crosslinks, for example between arginine residues of the same polypeptide or crosslinking between peptides, or crosslinking to another surface, or a combination thereof. By way of another example, polyarginine may have uses in hair and skin treatment where other such cationic polymers are commonly used.

In an embodiment the present invention describes a method whereby nitrogen is in effect continuously pulled from solution by an organism, concentrated into a soluble polymer, secreted, and then collected from solution by soil-amenable cation exchange media so as to drive the flux of nitrogen from the feed stream into a concentrated, usable fertilizer or arginine-rich product.

Thus, the present invention includes use of arginine-rich protein as fertilizer wherein said protein is generally greater than 60% arginine. The arginine-rich proteins are polymers generally between 2 and 400 amino acids in length, but that may be larger in order to facilitate secretion by the cell, and/or in order to facilitate aggregation and or collection outside of the cell, and/or to facilitate formulation, uptake as fertilizer by cells and/or slowed nitrogen release by degrading organisms or enzymes.

The arginine-rich protein or polypeptide may have the % arginine, composition and amino acid sequence and/or length of the arginine-rich protein modified to increase or decrease the rate of nitrogen release from the arginine-rich protein when used as a fertilizer; and/or to increase passive diffusion or active secretion of the arginine-rich protein to the outside of the cell.

The organisms producing the arginine-rich proteins can be nitrogen-fixing organisms, such as, for example, cyanobacteria or other photosynthetic organisms such as non-sulfur purple bacteria or a mixture of nitrogen-fixing organisms and possibly complex mixtures of other organisms so as to facilitate the production of arginine-rich proteins.

Optionally, the nitrogen-fixing organisms are genetically modified or otherwise selected to increase the level of nitrogen fixation.

The description of the various embodiments has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiments described and shown in the figures were chosen and described in order to explain the principles of the invention, the practical application, and to enable others of ordinary skill in the art to understand the invention for various embodiments with various modifications as are suited to the particular use contemplated. All references cited herein are incorporated in their entirety by reference.

EXAMPLES

Example 1

Growth comparison of an *E. coli* arginine auxotroph on arginine (FIG. 1) and polyarginine (FIG. 2). *E. coli* strain NK5992 was pre-grown on arginine in M9 medium, spun down and resuspended in a 60-fold dilution of fresh M9 containing the indicated levels of arginine or synthesized polyarginine ($Arg_{70}$; Sigma, 15-70KD, 80-400 amino acids). Cells were grown in triplicate at 37° C. on a 96-well plate with measurement at 600 nm using a Tecan InfiniteM200 pro.

Example 2

Figure 3:
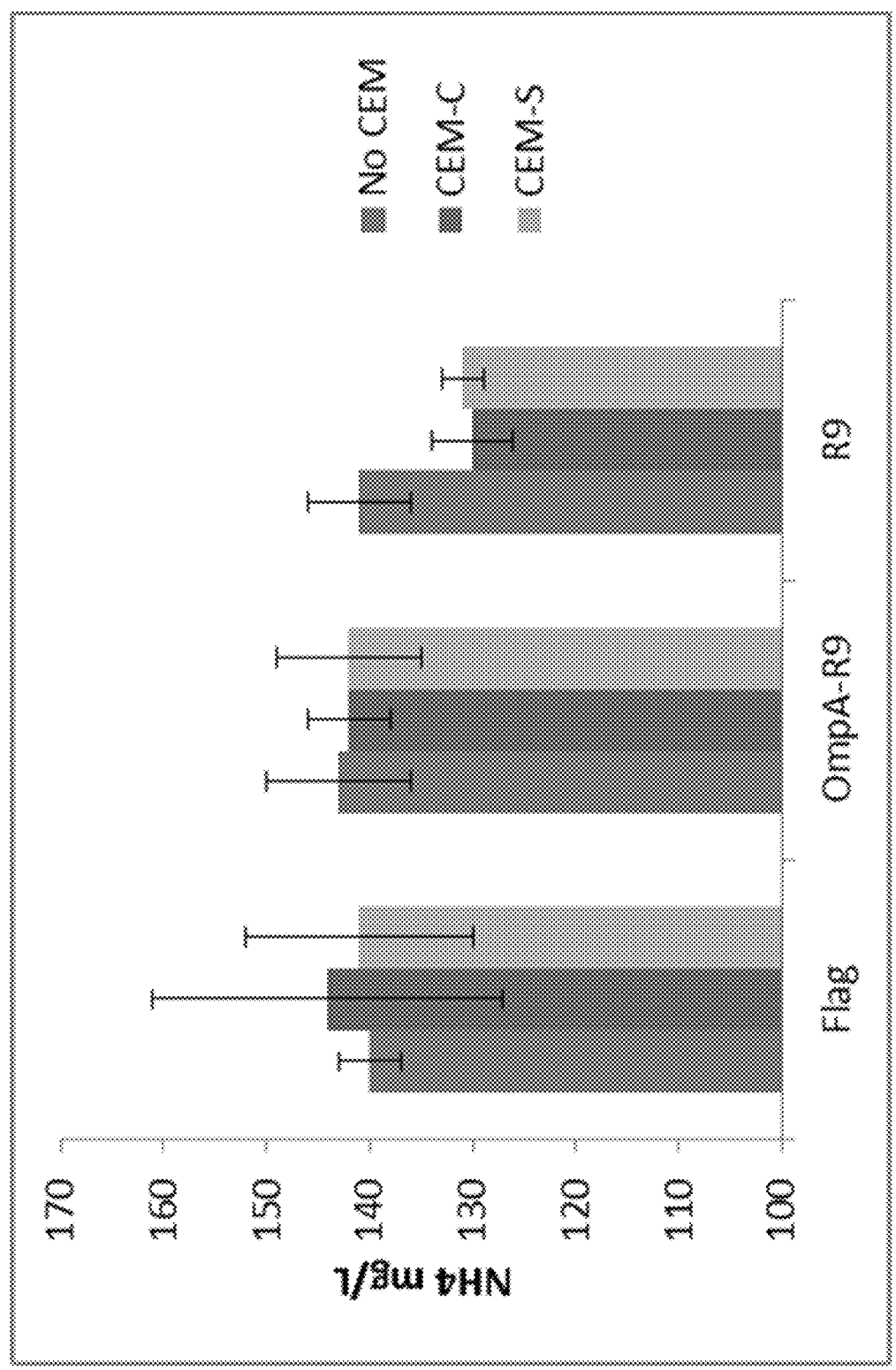
FIG. 3 shows the increased uptake of $NH_4$ from growth medium by *E. coli* cells when the cells are producing polyarginine. This only is true when cation exchange media is present, indicating that the polyarginine produced draws $NH_4$ from solution by deposition of the $NH_4$ as polyarginine on the cation exchange media.

Decreases in ammonium concentration is dependent upon both cation exchange resin in the growth media and *E. coli* containing an R9 gene. *E. coli* S17-1 cells were transformed either with the control pFLAG-CTS plasmid (the OmpA signal sequence followed by a neutral FLAG peptide), the pFLAG-CTS plasmid containing the OmpA R9 sequence (the OmpA signal sequence followed by nine arginines and a stop codon) or just the R9 sequence. One ml of cells were grown to an OD of 0.3 600 nm in M9 medium containing 0.2% glucose and 340 mg/L ammonium as ammonium chloride and then induced with 1 mg/ml IPTG. Where indicated, cation exchange media (CEM) was added as 24 micro equivalents (approximately 15 µl of swelled resin) of either Whatman Express-ion C (carboxymethyl cellulose) or Whatman Express-ion S (sulphoxyethyl cellulose), and where the CEM had been preconditioned overnight in M9 medium. The initial M9 medium had about 55 microequivalents of NH4+ per ml. Cells were grown in biological triplicate, with shaking, for 48 hours at 37° C. Ammonium levels for each replicate were detected in technical duplicate using a YSI 7100MBS. Most error resulted from between-biological replicates rather than technical measurements. Addition of CEM to M9 medium alone showed a slight lowering of measured ammonium, but this lowering was well within analysis error. Error bars were calculated using one standard deviation from the mean. See FIG. 3. Per each data set, the first column: No CEM; second column: CEM-C; third column, CEM-S.

Example 3

Figure 4:
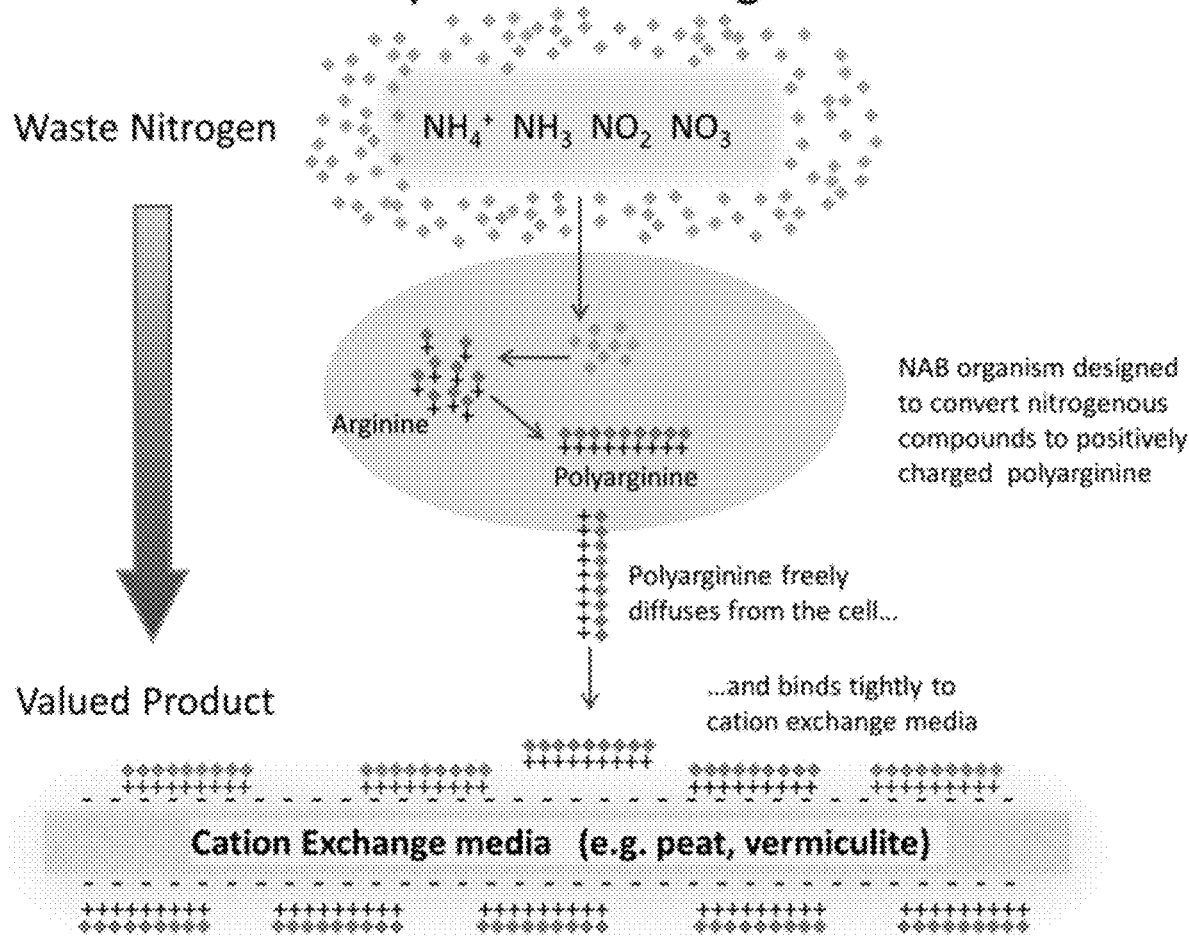
FIG. 4 shows an overview of Nitrogen Arginine Biorecovery (NAB)

FIG. 4 shows a schematic of a Nitrogen-Arginine Biorecovery (NAB) Process. Nitrogenous compounds are taken up by cells, converted to highly positively-charged polyarginine molecules and trapped on cation exchange media. Through mass transfer nitrogen is depleted to very low levels in the surrounding medium. The polyarginine can either be recovered from the cation exchange media, or the polyarginine-coated media can be used directly as a soil amendment.

Example 4

See FIG. 6. Polyarginine and arginine were shown to act as a fertilizer as well as a stimulant for germination. Approximately 300 *Arabidopsis thaliana* seeds were soaked in 75% ethanol for one minute, then soaked in 10% bleach, 0.02% TRITON×100 for five minutes, then washed five times with sterile water. The seeds were then resuspended in about 4 ml water, and dispensed into 30 Eppendorf tubes at approximately 100 microliters per tube, for a total of 8-9 seeds per tube. Test conditions included either water, 1× or 0.1×MS medium (Caisson; MSPA0910, MS medium with added macro and micronutrients, Vitamins and glycine; 1× media is nitrogen replete with a final glycine content of 2 mg/mL and $NH_4NO_3$ at 1.6 g/L), and either zero, 10 µg/ml, 30 µg/ml, 100 µg/ml, and 300 µg/ml polyarginine ($Arg_{70}$; Sigma, 15-70 KD, 80-400 amino acids) or arginine. Growth conditions were 75 $\mu E\ m^{-1}\ s^{-1}$ LED light as detected at level with the seed through the plastic Eppendorf cap, with shaking at 200 RPM at 21° C. Wet weight total biomass was determined on Day 5, germination profiles were determined on day 4. Root length and stem lengths are in mm.

Results: At day 4. Arginine and polyarginine were shown to have increased percentages of *Arabidopsis thaliana* germination by up to 9-fold (see column: x-fold germination) in a dose-dependent manner when the seeds were grown in 1× MS nitrogen-replete media. The arginine had the same relative effect on percent germination when added to 0.1× MS medium. The optimal level of either arginine or polyarginine was 100 µg/ml. At day 5, arginine and polyarginine were shown to have increased *Arabidopsis thaliana* biomass production by up to 4-fold (see column: x-fold biomass) in a dose-dependent manner. Again, the optimal level of arginine or polyarginine was 100 µg/ml. This is of particular note because the commercial SM medium used was designed with sufficient $NH_4NO_3$ for plant growth. Using 100 µg/ml polyarginine in water, the seeds showed a large amount of root growth that was not found in the case of using arginine. It is not known what caused this or the isolated case of increased growth at 0.1× MS using 10 µg/ml polyarginine.

Example 5

See FIG. 7 and FIG. 5. The binding of cobalt to cation exchange resin CM sepharose was shown to be inhibited by the presence of polyarginine but not by the presence of arginine. Solutions were made having a final level of 2.5 µM $CoCl_2$, 0.95 µM of either Arginine or polyarginine ($Arg_{70}$, Sigma, 15-70 KD, 80-400 amino acids) and 0.65 µM meq of CM seph (5 µl wet volume). This represents competitive conditions, having 2.6-fold excess cobalt over the arginine/polyarginine, and saturation of the CM sepharose with cations. The $CoCl_2$ and inhibitor (either arginine, polyarginine, or water) were mixed prior to adding the sepharose. The final solution had a $CoCl_2$ concentration of 25 mM. After sitting for 1 minute the sepharose was washed 2× with water to remove excess cobalt and inhibitor. The cobalt was then stripped from the column material with 50 µl of 50 mM EDTA and this cobalt-containing wash was made basic with 50 µl of 50 mM NaOH. The cobalt-containing wash was then monitored on a DU800 spectroscope at 463 nm wavelength for the data of Table 2 (FIG. 7), and from 350 nm to 650 nm for FIG. 5. The data of FIG. 5 and FIG. 7 were from separate experiments acquired on two different days.

Results: Under the conditions used, polyarginine outcompeted cobalt >2:1 for binding to CM sepharose when the number of anionic sites on the CM sepharose was limiting. This occurred even though the cobalt was in a 2.6-fold excess over the polyarginine (molar excess as calculated on a per arginine monomer basis; the excess $Co^{++}$ over polyarginine on a molar basis was at least 210-fold since the polyarginine used had 80-400 arginine residues per molecule). Arginine did not compete with cobalt for the CM sepharose but instead, for unknown reasons, enhanced the binding of cobalt to the resin.

Example 6

E. coli S17-1 cells were transformed either with the pFLAG-CTS plasmid containing the OmpA R9 sequence (the OmpA signal sequence followed by nine arginines and a stop codon, final product (AQASRRRRRRRRR—SEQ ID NO: 13)) or the same construct without the OmpA signal sequence (MR9). As a control, the same system was used with just the 39-amino acid OmpA control FLAG peptide sequence. Cells were grown to an OD of 0.3 in minimal media at 0.4%, 0.8%, or 1.6% glycerol and 340 mg/L ammonium and then induced with IPTG at 30° C. CM-sepharose, a cation exchange media (CEM) was included during the incubation at 5% of the total solution volume. At 2 and 4 days of growth post IPTG induction a sample of the cation exchange media was washed with 0.2M NaOH and then 10 ul of the CEM was loaded directly onto a PAGE gel after heating to 95 C in 1× gel loading buffer. The gel was stained with a Coomassie colloidal stain. Based on the two reference lanes OmpR9 was produced at a level of 1% of available $NH_4^+$ but only in the strain having R9 behind the secretory OmpA signal. See FIG. 13. There was very little contaminating protein, indicating that the purification and column wash technique gave pure product. There was increased product formation over time and at increasing glycerol concentrations.

OmpAR9 DNA coding sequence:

(SEQ ID NO: 14)
ATGAAAAAGACAGCTATCGCGATTGCAGTGGCACTGGCTGGTTTCGCTAC

CGTTGCGCAAGCTTCTCGACGCCGCCGTCGTCGCCGTCGCCGTTGA.

OmpAR9 initial peptide sequence (pre cleavage by bacteria) is

MKKTAIAIAVALAGFATVAQASRRRRRRRRR. (SEQ ID NO: 15)

OmpAR9 peptide sequence (the final, secreted product):

AQASRRRRRRRRR. (SEQ ID NO: 13)

In order to show bacterial colony secretion of polyarginine, the assay includes growth on minimal medium (no arginine) agar underlay of cells having constitutive GFP expression but being auxotrophic for arginine, therefore requiring an overlay of polyarginine-secreting colonies for growth. Green colonies correspond to growth of the underlay cells using polyarginine secreted by overlay cells. Red corresponds to all overlay colony types (no GFP). Plates were visualized on a Fluorochem Q using identical parameters. The next step with this screen is to differentiate polyarginine from arginine by including carboxypeptidase B in the overlay.

Example 7

Arginine was saturated onto Dowex 50wx8 CEM in water and washed with methanol (arginine is insoluble in methanol). Product was stripped from the CEM in anhydrous 2N NaOH/methanol at ~63° C. for 5' (arginine is soluble in NaOH/methanol at up to 35% by weight), and recrystallized at 4° C. The crystalline product was washed with methanol and dried, resulting in a very fine powder that was freely soluble in water. Overall yield averaged 90%, with a very high purity by thermal gravimetric analysis.

---

What is claimed is:

1. A method to increase conversion of nitrogen in a nitrogen-containing wastewater stream to an arginine-enriched polypeptide, comprising:
(a) supplying a nitrogen-containing wastewater stream;
(b) culturing an organism in the wastewater stream, wherein the organism is capable of producing an arginine-enriched polypeptide, to produce the arginine-enriched polypeptide;
(c) removing the produced arginine-enriched polypeptide from the wastewater stream to create a processed wastewater stream, wherein the processed wastewater stream has a lower nitrogen content; and
(d) supplying a plant with the produced arginine-enriched polypeptide from the wastewater stream, wherein the arginine-enriched polypeptide comprises greater than 51% arginine and increases the growth or production of the plant.

2. The method of claim 1, wherein the method of culturing the organism in the wastewater stream comprises:
(a) subjecting the wastewater stream to an at least partial nitrification/denitrification step, to produce a pretreated effluent;
(b) subjecting the pretreated effluent to an anaerobic digestion step to create a treated effluent; and
(c) subjecting the treated effluent to conditions which allow the organism to proliferate and/or express the arginine-enriched polypeptide.

3. The method of claim 2, wherein the method step further comprises adding a carbon-source to the nitrogen-containing waste stream, the pretreated effluent, or the treated effluent.

4. The method of claim 1, wherein the nitrogen-containing wastewater feed stream comprises a wastewater feed stream selected from the group consisting of a municipal wastewater feedstream, an agricultural wastewater feedstream, an industrial wastewater feedstream, and a holding pond/lagoon feedstream.

5. The method of claim 1, wherein the step of removing the produced arginine-enriched polypeptide from the wastewater stream to create a processed wastewater stream comprises flowing the effluent from the culturing step over a cation exchange material under conditions that allow binding of the arginine-enriched polypeptide to the cation exchange material.

6. The method of claim 5, wherein the processed wastewater stream is recycled into the process.

7. The method of claim 4 wherein the cation exchange material is a commercially available cation exchange media, peat, diatomaceous earth, compost, clay, soil, or combinations thereof.

8. The method of claim 5, wherein the method further comprises eluting the bound arginine-enriched polypeptide from the material and collecting the eluted arginine-enriched polypeptide.

9. The method of claim 5, wherein the produced arginine-enriched polypeptide remains bound to the cation exchange media.

10. The method of claim 1, wherein the arginine-enriched polypeptide is polyarginine.

11. The method of claim 1, wherein the arginine-enriched polypeptide comprises:
(a) a cleavage protein product comprising greater than 60% arginine;
(b) a polymer of between 2 and 400 amino acids in length; and/or
(c) a polypeptide selected from the group consisting of $Arg_{5-20}$, $Met\text{-}Arg_{5-20}$, $Met\text{-}x\text{-}Arg_{5-20}$, $Met(\text{-}Arg_{5-20}\text{-}x)_y$, $sig\text{-}Arg_{5-20}$, $Met\text{-}sig\text{-}Arg_{5-20}$, $Met\text{-}Sig\text{-}(\text{-}Arg_{5-20}\text{-}x)_z$, $Sig\text{-}(\text{-}Arg_{5-20}\text{-}x)_z$, $Arg_{5-20}$, $Met\text{-}Arg_{5-20}$, $Met\text{-}x\text{-}Arg_{5-20}$, $Met(\text{-}Arg_{5-20}\text{-}x)_y$, $sig\text{-}Arg_{5-20}$, $Met\text{-}sig\text{-}Arg_{5-20}$, $Met\text{-}Sig\text{-}(\text{-}Arg_{5-20}\text{-}x)_z$, $Sig\text{-}(\text{-}Arg_{5-20}\text{-}x)_z$, and a polypeptide mixture with an average size of between 5 and 20 arginines.

12. The method of claim 1, wherein the arginine-enriched polypeptide includes a secretory sequence which is capable of directing secretion outside of the organism.

13. The method of claim 1, wherein the arginine-enriched polypeptide producing organism is modified to i) increase arginine-rich protein production; ii) down-regulate levels of arginine export genes; iii) down-regulate genes that degrade arginine-containing polypeptides; iv) reduce the amount of other arginine-containing compounds; v) down-regulate arginine catabolism genes; vi) down-regulation of an arginine synthesis feedback inhibition gene; or vii) a combination of the above.

14. The method of claim 13, wherein arginine-rich protein production by the arginine-enriched polypeptide producing organism is increased by upregulating argininosuccinate lyase; wherein an arginine export gene is argO; wherein a gene that degrades an arginine-containing polypeptide is carboxypeptidase B; wherein another arginine-containing compound is cyanophycin; wherein the arginine catabolism gene is arginase; and wherein the arginine synthesis feedback inhibition gene is argA.

15. The method of claim 13, wherein the modified arginine-enriched polypeptide producing organism is selected by screening the organism, wherein the screening step comprises culturing the organism with a reagent that indicates the presence of arginine, wherein the reagent comprises Sakaguchi reagent, acid dyes and fluorophores.

16. The method of claim 1, wherein the method further comprises supplying seeds, grafts or plant cell culture with the produced arginine-enriched polypeptide from the wastewater stream, wherein the produced arginine-enriched polypeptide increases the growth or production of the plant.

17. A method to make a composition comprising an arginine-enriched polypeptide fertilizer, comprising;
(a) supplying a nitrogen-containing wastewater stream;
(b) culturing an organism in the waste stream that produces an arginine-enriched polypeptide to produce the arginine-enriched polypeptide;
(c) flowing the effluent from the culturing step over a cation exchange material under conditions that allow binding of the arginine-enriched polypeptide to the cation exchange material, wherein the produced arginine-enriched polypeptide is bound to the cation exchange media; and
(d) eluting the bound arginine-enriched polypeptide from the material and collecting the eluted arginine-enriched polypeptide to form the arginine-enriched polypeptide fertilizer.

18. The method of claim 17, wherein the eluted arginine-enriched polypeptide is bound to a cation exchange material selected from the group consisting of peat, diatomaceous earth, compost, clay, soil, or commercially available cation exchange media, and combinations thereof to form the arginine-enriched polypeptide fertilizer.

19. A method to increase the growth or production of a plant comprising:
(a) supplying a nitrogen-containing wastewater stream;
(b) culturing an organism in the waste stream that produces an arginine-enriched polypeptide to produce the arginine-enriched polypeptide;
(c) flowing the effluent from the culturing step over a cation exchange material under conditions that allow binding of the arginine-enriched polypeptide to the cation exchange material, wherein the produced arginine-enriched polypeptide is bound to the cation exchange media;
(d) eluting the bound arginine-enriched polypeptide from the material and collecting the eluted arginine-enriched polypeptide; and
(e) applying at least a portion of the arginine-enriched polypeptide to a plant in a growth phase or a production phase, wherein the arginine-enriched polypeptide comprises greater than 51% arginine and increases the growth or production of the plant.

* * * * *

UNITED STATES PATENT AND TRADEMARK OFFICE
CERTIFICATE OF CORRECTION

Page 1 of 1

PATENT NO. : 10,934,224 B2
APPLICATION NO. : 16/040327
DATED : March 2, 2021
INVENTOR(S) : Matt S. A. Wecker It is certified that error appears in the above-identified patent and that said Letters Patent is hereby corrected as shown below:

In the Claims

Column 29, Claim 7, Line 64, replace "4" with --5--.

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 15

<210> SEQ ID NO 1
<211> LENGTH: 10
<212> TYPE: PRT
<213> ORGANISM: Artificial
<220> FEATURE:
<223> OTHER INFORMATION: Synthetic construct

<400> SEQUENCE: 1

Arg Arg Arg Arg Arg Arg Arg Arg Lys Arg
1               5                   10

<210> SEQ ID NO 2
<211> LENGTH: 10
<212> TYPE: PRT
<213> ORGANISM: Artificial
<220> FEATURE:
<223> OTHER INFORMATION: Synthetic construct

<400> SEQUENCE: 2
```

Arg Arg Arg Arg Arg Arg Arg His Arg Arg
1               5                   10

<210> SEQ ID NO 3
<211> LENGTH: 16
<212> TYPE: PRT
<213> ORGANISM: Artificial
<220> FEATURE:
<223> OTHER INFORMATION: Synthetic construct

<400> SEQUENCE: 3

Arg Arg Arg Arg Arg Arg Lys Lys Lys Lys Gly Arg Arg Arg Arg Arg
1               5                   10                  15

<210> SEQ ID NO 4
<211> LENGTH: 8
<212> TYPE: PRT
<213> ORGANISM: Artificial
<220> FEATURE:
<223> OTHER INFORMATION: Synthetic construct

<400> SEQUENCE: 4

Arg Arg Arg Arg Arg Arg Arg Arg
1               5

<210> SEQ ID NO 5
<211> LENGTH: 8
<212> TYPE: PRT
<213> ORGANISM: Artificial
<220> FEATURE:
<223> OTHER INFORMATION: Synthetic construct

<400> SEQUENCE: 5

Arg Arg Arg Arg Arg Arg Arg Arg
1               5

<210> SEQ ID NO 6
<211> LENGTH: 9
<212> TYPE: PRT
<213> ORGANISM: Artificial
<220> FEATURE:
<223> OTHER INFORMATION: Synthetic construct

<400> SEQUENCE: 6

Arg Arg Arg Arg Arg Arg Arg Lys Arg
1               5

<210> SEQ ID NO 7
<211> LENGTH: 9
<212> TYPE: PRT
<213> ORGANISM: Artificial
<220> FEATURE:
<223> OTHER INFORMATION: Synthetic construct

<400> SEQUENCE: 7

Arg Arg Arg Arg Arg Lys Arg Arg Arg
1               5

<210> SEQ ID NO 8
<211> LENGTH: 9
<212> TYPE: PRT
<213> ORGANISM: Artificial
<220> FEATURE:
<223> OTHER INFORMATION: Synthetic construct

<400> SEQUENCE: 8

Arg Arg Arg Arg Arg Gln Arg Arg Arg

<210> SEQ ID NO 9
<211> LENGTH: 9
<212> TYPE: PRT
<213> ORGANISM: Artificial
<220> FEATURE:
<223> OTHER INFORMATION: Synthetic construct

<400> SEQUENCE: 9

Arg Gln Arg Arg Arg Arg Arg Arg Arg
1               5

<210> SEQ ID NO 10
<211> LENGTH: 12
<212> TYPE: PRT
<213> ORGANISM: Artificial
<220> FEATURE:
<223> OTHER INFORMATION: Synthetic construct

<400> SEQUENCE: 10

Arg Arg Arg Arg Arg Met Pro Glu Arg Arg Arg Arg
1               5                   10

<210> SEQ ID NO 11
<211> LENGTH: 8
<212> TYPE: PRT
<213> ORGANISM: Artificial
<220> FEATURE:
<223> OTHER INFORMATION: Synthetic construct

<400> SEQUENCE: 11

Arg Arg Arg Arg Arg Arg Lys Arg
1               5

<210> SEQ ID NO 12
<211> LENGTH: 10
<212> TYPE: PRT
<213> ORGANISM: Artificial
<220> FEATURE:
<223> OTHER INFORMATION: Synthetic construct

<400> SEQUENCE: 12

Arg Arg Arg His Arg Arg Pro Arg Arg Arg
1               5                   10

<210> SEQ ID NO 13
<211> LENGTH: 13
<212> TYPE: PRT
<213> ORGANISM: Artificial
<220> FEATURE:
<223> OTHER INFORMATION: Synthetic construct

<400> SEQUENCE: 13

Ala Gln Ala Ser Arg Arg Arg Arg Arg Arg Arg Arg Arg
1               5                   10

<210> SEQ ID NO 14
<211> LENGTH: 96
<212> TYPE: DNA
<213> ORGANISM: Artificial
<220> FEATURE:
<223> OTHER INFORMATION: Synthetic construct

<400> SEQUENCE: 14
atgaaaaaga cagctatcgc gattgcagtg gcactggctg gtttcgctac cgttgcgcaa      60

```
gcttctcgac gccgccgtcg tcgccgtcgc cgttga                            96
```

<210> SEQ ID NO 15
<211> LENGTH: 31
<212> TYPE: PRT
<213> ORGANISM: Artificial
<220> FEATURE:
<223> OTHER INFORMATION: Synthetic construct

<400> SEQUENCE: 15

Met Lys Lys Thr Ala Ile Ala Ile Ala Val Ala Leu Ala Gly Phe Ala
1               5                   10                  15

Thr Val Ala Gln Ala Ser Arg Arg Arg Arg Arg Arg Arg Arg
            20                  25                  30